US012649797B2

(12) United States Patent
Curran et al.

(10) Patent No.: US 12,649,797 B2
(45) Date of Patent: Jun. 9, 2026

(54) HUMAN 4-1BB AGONIST ANTIBODIES AND METHODS OF USE THEREOF

(71) Applicant: Board of Regents, The University of Texas System, Austin, TX (US)

(72) Inventors: Michael A. Curran, Houston, TX (US); Renee Chin, Houston, TX (US); Marie-Andrée Forget, Houston, TX (US); Chantale Bernatchez, Houston, TX (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 928 days.

(21) Appl. No.: 17/904,459

(22) PCT Filed: Feb. 17, 2021

(86) PCT No.: PCT/US2021/018276
§ 371 (c)(1),
(2) Date: Aug. 17, 2022

(87) PCT Pub. No.: WO2021/167915
PCT Pub. Date: Aug. 26, 2021

(65) Prior Publication Data
US 2023/0092390 A1     Mar. 23, 2023

Related U.S. Application Data

(60) Provisional application No. 62/977,658, filed on Feb. 17, 2020.

(51) Int. Cl.
| | |
|---|---|
| *A61K 51/10* | (2006.01) |
| *A61K 35/17* | (2025.01) |
| *A61K 39/395* | (2006.01) |
| *A61K 45/06* | (2006.01) |
| *A61K 47/68* | (2017.01) |
| *A61P 35/00* | (2006.01) |
| *C07K 16/28* | (2006.01) |

(52) U.S. Cl.
CPC .......... *C07K 16/2878* (2013.01); *A61K 35/17* (2013.01); *A61K 39/3955* (2013.01); *A61K 45/06* (2013.01); *A61K 47/6849* (2017.08); *A61K 51/1033* (2013.01); *A61P 35/00* (2018.01); *C07K 2317/21* (2013.01); *C07K 2317/24* (2013.01)

(58) Field of Classification Search
CPC ............... A61K 47/6849; A61K 35/17; A61K 39/3955; A61K 45/06; A61K 51/1033; A61P 35/00
See application file for complete search history.

(56) References Cited

U.S. PATENT DOCUMENTS

| | | | |
|---|---|---|---|
| 5,827,642 | A | 10/1998 | Riddell et al. |
| 10,308,709 | B2 | 6/2019 | Tu et al. |
| 2004/0058445 | A1* | 3/2004 | Ledbetter ............. C12N 5/0636 |
| | | | 435/372 |
| 2008/0112951 | A1 | 5/2008 | Phalipon et al. |
| 2009/0098140 | A1 | 4/2009 | Grompe et al. |
| 2014/0086913 | A1 | 3/2014 | Smith et al. |
| 2014/0154254 | A1 | 6/2014 | Kannan et al. |
| 2015/0133640 | A1 | 5/2015 | Blein et al. |
| 2015/0147333 | A1 | 5/2015 | Storm et al. |
| 2017/0044496 | A1 | 2/2017 | Sarnaik et al. |
| 2023/0106973 | A1 | 4/2023 | Forget et al. |

FOREIGN PATENT DOCUMENTS

| | | | |
|---|---|---|---|
| WO | WO 2010/113117 A2 | 10/2010 |
| WO | WO 2010/138803 A2 | 12/2010 |
| WO | WO 2015/189638 A2 | 12/2015 |
| WO | WO 2016/131125 A1 | 8/2016 |
| WO | WO 2017/205745 A1 | 11/2017 |
| WO | WO 2019/136459 A1 | 7/2019 |
| WO | WO 2019/141268 A1 | 7/2019 |
| WO | WO 2019/190579 A1 | 10/2019 |
| WO | WO 2019/210131 A1 | 10/2019 |
| WO | WO 2020/011968 A1 | 1/2020 |

OTHER PUBLICATIONS

Bartkowiak, T. et al., "4-1BB agonists: multi-potent potentiators of tumor immunity," *Frontiers in Oncology*, 5.117 (2015): 1-16.
Chacon, J. A. et al., "Co-Stimulation through 4-1BB/CD137 Improves the Expansion and Function of CD8+ Melanoma Tumor-Infiltrating Lymphocytes for Adoptive T-Cell Therapy," *PLOS One*, 8.4 (2013): e60031, 1-14.
Chapuis, A. G. et al., "Transferred Melanoma-Specific CD8+ T Cells Persist, Mediate Tumor Regression and Acquire Central Memory Phenotype," *PNAS*, 109.12 (2012): 4592-4597.
Creasy, C. A. et al., "Exposure to anti-PD-1 causes functional differences in tumor-infiltrating lymphocytes in rare solid tumors," *Eur J Immunol*, 49 (2019): 2245-2251.
Dudley, M. E. et al. "Adoptive cell transfer therapy following non-myeloablative but lymphodepleting chemotherapy for the treatment of patients with refractory metastatic melanoma," *Journal of Clinical Oncology*, 23.10 (2005): 2346-2357.
Extended European Search Report issued in European Patent Application No. 21757958.0, dated Jun. 4, 2024.
Forget, M.-A. et al., "A Novel Method to Generate and expand Clinical-Grade, Genetically Modified, tumor-Infiltrating Lymphocytes," *Frontiers in Immunology*, 8.908 (2017): 1-8.
Forget, M. A. et al., "Prospective Analysis of Adoptive TIL Therapy in Patients with Metastatic Melanoma: Response, Impact of Anti-CTLA4, and Biomarkers to Predict Clinical Outcome," *Clin Cancer Res*, 24.18 (2018): 4416-4428.

(Continued)

*Primary Examiner* — Nelson B Moseley, II
*Assistant Examiner* — Dennis J Sullivan
(74) *Attorney, Agent, or Firm* — pH IP Law

(57) ABSTRACT
Isolated or recombinant monoclonal antibodies that bind to 4-1BB are provided. In some cases, antibodies of the embodiments can be used for the detection, diagnosis and/or therapeutic treatment of human diseases, such as cancer.

19 Claims, 7 Drawing Sheets

Specification includes a Sequence Listing.

(56)                    References Cited

OTHER PUBLICATIONS

Grimm, E. A. et al., "Characterization of interleukin-2-initiated versus OKT3-initiated human tumor-infiltrating lymphocytes from glioblastoma multiforme: growth characteristics, cytolytic activity, and cell phenotype," *Cancer Immunol Immunother.*, 32 (1991): 391-399.

Harao, M. et al., "4-1BB-enhanced expansion of CD8+ TIL from triple-negative breast cancer unveils mutation-specific CD8+ T cells," *Cancer Immunol Res.*, 5.6 (2017): 439-445.

Lutsiak, M. E. C. et al., "Inhibition of CD4($^+$)25$^+$ T regulatory cell function implicated in enhanced immune response by low-dose cyclophosphamide," *Blood*, 105.7 (2005): 2862-2868.

Maguire, H. C. et al., "Enhancement of dinitrochlorobenzene (DNCB) contact sensitization by cyclophosphamide in the guinea pig," *The Journal of Investigative Dermatology*, 48.1 (1967): 39-43.

Mardiana, S. et al., "A Multifunctional Role for Adjuvant Anti-4-1BB Therapy in Augmenting Antitumor Response by Chimeric Antigen Receptor T Cells," *Cancer Research*, 77.6 (2017): 1296-1309.

Martinez, O. M. et al., "IL-4 inhibits IL-2 receptor expression and IL-2-dependent proliferation of human T cell," *The Journal of Immunology*, 144 (1990): 2211-2215.

Nielson, M. et al., "Preclinical development of tumor-infiltrating lymphocyte (TIL) based adoptive cell transfer (ACT) immunotherapy for patients with sarcoma and the potential benefit of anti-CD137 stimulation," *J Clin Oncol.*, 35 (2017): abstract No. e14545.

Partial European Search Report issued in European Patent Application No. 21757958.0, dated Mar. 11, 2024.

PCT International Search report and Written Opinion issued in International Patent Application No. PCT/US2021/018276, mailed Jun. 23, 2021.

PCT International Preliminary Report on Patentability issued in International Patent Application No. PCT/US2021/018276, mailed Sep. 1, 2022.

PCT International Search report and Written Opinion issued in International Patent Application No. PCT/US2021/018252, mailed May 14, 2021.

PCT International Preliminary Report on Patentability issued in International Patent Application No. PCT/US2021/018252, mailed Sep. 1, 2022.

Qi, X. et al., "Optimization of 4-1BB antibody for cancer immunotherapy by balancing agonistic strength with FcγR affinity," *Nature Communications*, 10 (2019): 2141, 1-11.

Quezada, S. A. et al., "CTLA4 blockade and GM-CSF combination immunotherapy alters the intratumor balance of effector and regulatory T cells," *The Journal of Clinical Investigation*, 116.7 (2006): 1935-1945.

Rabu, C. et al., "Production of Recombinant Human Trimeric CD137L (4-1BBL)," *The Journal of Biological Chemistry*, 280.50 (2005): 41472-41481.

Radvanyi, L. G. et al., "Specific lymphocyte subsets predict response to adoptive cell therapy using expanded autologous tumor-infiltrating lymphocytes in metastatic melanoma patients," *Clin Cancer Res*, 18.24 (2012): 6758-6770.

Sakellariou-Thompson, D et al., "4-1BB agonist focuses CD8+ tumor-infiltrating T-cell growth into a distinct repertoire capable of tumor recognition in pancreatic cancer," *Clin Cancer Res.*, 23.23 (2017): 7263-7275.

Sakellariou-Thompson, D. et al., "Potential clinical application of tumor-infiltrating lymphocyte therapy for ovarian epithelial cancer prior or post-resistance to chemotherapy," *Cancer Immunology, Immunotherapy*, 68 (2019): 1747-1757.

Shah, P. et al., "Combined IL-2, agonistic CD3 and 4-1BB stimulation preserve clonotype hierarchy in propagated non-small cell lung cancer tumor-infiltrating lymphocytes," *J Immunother Cancer*, 10 (2022): e003082, 1-14.

Somerville, R. P. T. et al., "Clinical scale rapid expansion of lymphocytes for adoptive cell transfer therapy in the WAVE® bioreactor," *The Journal of Translational Medicine*, 10.69 (2012): 1-11.

Sutmuller, R. P. et al., "Synergism of cytotoxic T lymphocyte-associated antigen 4 blockade and depletion of CD25(+) regulatory T cells in antitumor therapy reveals alternative pathways for suppression of autoreactive cytotoxic T lymphocyte responses," *J Exp Med.*, 194.6 (2001): 823-832.

Tavera, R. J. et al., "Utilizing T-cell Activation Signals 1, 2, and 3 for Tumor-infiltrating Lymphocytes (TIL) Expansion: The Advantage Over the Sole Use of Interleukin-2 in Cutaneous and Uveal Melanoma," *J Immunother.*, 41.9 (2018): 399-405.

Tsoukas, C. D. et al., "Activation of resting T lymphocytes by anti-CD3 (T3) antibodies in the absence of monocytes," *The Journal of Immunology*, 135 (1985): 1719-1723.

Vinay, D. S. et al., "Immunotherapy of Cancer with 4-1BB," *Molecular Cancer Therapeutics*, 11.5 (2012): 1062-1070.

Vormittag, P. et al., "A guide to manufacturing CAR T cell therapies," *Current Opinion in Biotechnology*, 53 (2018): 164-181.

Weber, J. et al., "White Paper on Adoptive Cell Therapy for Cancer with Tumor-Infiltrating Lymphocytes: A Report of the CTEP Subcommittee on Adoptive Cell Therapy," *Clinical Cancer Research*, 17.7 (2011): 1664-1673.

* cited by examiner mAb 271-49A   EC50 = 0.001316 ug/ml mAb 271-138   EC50 = 0.004709 ug/ml mAb 271-54     EC50 = 0.01602 ug/ml mAb 271-111A EC50 = 0.01394 ug/ml mAb 271-151A EC50 = 0.1022 ug/ml

SEQUENCE LISTING

<160> NUMBER OF SEQ ID NOS: 64

<210> SEQ ID NO 1
<211> LENGTH: 429
<212> TYPE: DNA
<213> ORGANISM: Artificial sequence
<220> FEATURE:
<223> OTHER INFORMATION: Synthetic antibody

<400> SEQUENCE: 1

```
gagttccagc tgcagcagtc tggacctgag ctggtgaagc ctggcgcttc agtgaagata      60
tcctgcaagg cttctggtta ctcattcact gactacaaca tgaactgggt gaagcagagc     120
aatggaaaga gccttgagtg gattggagta attaatccta actatggtac tactagctac     180
aatcagaagt tcaagggcaa ggccacattt actgtagacc aatcttccag cacagcctac     240
atgcagctca cagcctgac atctgaggac tctgcagtct attactgtgc aagatccccg      300
gtagaggact actttgacta ctggggccaa ggcaccactc tcacagtctc ctcagccaaa     360
acaacagccc catcggtcta tccactggcc cctgtgtgtg gaggtacaac tggctcctcg     420
gtgactcta                                                            429
```

<210> SEQ ID NO 2
<211> LENGTH: 143
<212> TYPE: PRT
<213> ORGANISM: Artificial sequence
<220> FEATURE:
<223> OTHER INFORMATION: Synthetic antibody -continued

```
<400> SEQUENCE: 2

Glu Phe Gln Leu Gln Gln Ser Gly Pro Glu Leu Val Lys Pro Gly Ala
1               5                   10                  15

Ser Val Lys Ile Ser Cys Lys Ala Ser Gly Tyr Ser Phe Thr Asp Tyr
                20                  25                  30

Asn Met Asn Trp Val Lys Gln Ser Asn Gly Lys Ser Leu Glu Trp Ile
            35                  40                  45

Gly Val Ile Asn Pro Asn Tyr Gly Thr Thr Ser Tyr Asn Gln Lys Phe
        50                  55                  60

Lys Gly Lys Ala Thr Phe Thr Val Asp Gln Ser Ser Ser Thr Ala Tyr
65                  70                  75                  80

Met Gln Leu Asn Ser Leu Thr Ser Glu Asp Ser Ala Val Tyr Tyr Cys
                85                  90                  95

Ala Arg Ser Pro Val Glu Asp Tyr Phe Asp Tyr Trp Gly Gln Gly Thr
                100                 105                 110

Thr Leu Thr Val Ser Ser Ala Lys Thr Thr Ala Pro Ser Val Tyr Pro
            115                 120                 125

Leu Ala Pro Val Cys Gly Gly Thr Thr Gly Ser Ser Val Thr Leu
    130                 135                 140

<210> SEQ ID NO 3
<211> LENGTH: 8
<212> TYPE: PRT
<213> ORGANISM: Artificial sequence
<220> FEATURE:
<223> OTHER INFORMATION: Synthetic antibody

<400> SEQUENCE: 3

Gly Tyr Ser Phe Thr Asp Tyr Asn
1               5

<210> SEQ ID NO 4
<211> LENGTH: 24
<212> TYPE: DNA
<213> ORGANISM: Artificial sequence
<220> FEATURE:
<223> OTHER INFORMATION: Synthetic antibody

<400> SEQUENCE: 4
ggttactcat tcactgacta caac                                           24

<210> SEQ ID NO 5
<211> LENGTH: 8
<212> TYPE: PRT
<213> ORGANISM: Artificial sequence
<220> FEATURE:
<223> OTHER INFORMATION: Synthetic antibody

<400> SEQUENCE: 5

Ile Asn Pro Asn Tyr Gly Thr Thr
1               5

<210> SEQ ID NO 6
<211> LENGTH: 24
<212> TYPE: DNA
<213> ORGANISM: Artificial sequence
<220> FEATURE:
<223> OTHER INFORMATION: Synthetic antibody

<400> SEQUENCE: 6
attaatccta actatggtac tact                                           24
```

<210> SEQ ID NO 7
<211> LENGTH: 11
<212> TYPE: PRT
<213> ORGANISM: Artificial sequence
<220> FEATURE:
<223> OTHER INFORMATION: Synthetic antibody

<400> SEQUENCE: 7

Ala Arg Ser Pro Val Glu Asp Tyr Phe Asp Tyr
1               5                   10

<210> SEQ ID NO 8
<211> LENGTH: 33
<212> TYPE: DNA
<213> ORGANISM: Artificial sequence
<220> FEATURE:
<223> OTHER INFORMATION: Synthetic antibody

<400> SEQUENCE: 8
gcaagatccc cggtagagga ctactttgac tac                                 33

<210> SEQ ID NO 9
<211> LENGTH: 380
<212> TYPE: DNA
<213> ORGANISM: Artificial sequence
<220> FEATURE:
<223> OTHER INFORMATION: Synthetic antibody

<400> SEQUENCE: 9
gaaaatgtgc tcacccagtc tccagcaatc atgtctgcat ctccagggga aaaggtcacc     60
atgacctgca gggccaggtc aagtgtaagt tccagttact tgcactggta ccagcagaag    120
tcaggtgcct cccccaaact ctggatttat agcacatcca acttggcttc tggagtccct    180
gctcgcttca gtggcagtgg gtctgggacc tcttactctc tcacaatcag cagtgtggag    240
gctgaagatg ctgccactta ttactgccag cagtacagtg gttacccact catcacgttc    300
ggtgctggga ccaagctgga gctgaaacgg gctgatgctg caccaactgt atccatcttc    360
ccaccatcca gtgagcagtt                                               380

<210> SEQ ID NO 10
<211> LENGTH: 126
<212> TYPE: PRT
<213> ORGANISM: Artificial sequence
<220> FEATURE:
<223> OTHER INFORMATION: Synthetic antibody

<400> SEQUENCE: 10

Glu Asn Val Leu Thr Gln Ser Pro Ala Ile Met Ser Ala Ser Pro Gly
1               5                   10                  15

Glu Lys Val Thr Met Thr Cys Arg Ala Arg Ser Ser Val Ser Ser Ser
            20                  25                  30

Tyr Leu His Trp Tyr Gln Gln Lys Ser Gly Ala Ser Pro Lys Leu Trp
        35                  40                  45

Ile Tyr Ser Thr Ser Asn Leu Ala Ser Gly Val Pro Ala Arg Phe Ser
    50                  55                  60

Gly Ser Gly Ser Gly Thr Ser Tyr Ser Leu Thr Ile Ser Ser Val Glu
65                  70                  75                  80

Ala Glu Asp Ala Ala Thr Tyr Tyr Cys Gln Gln Tyr Ser Gly Tyr Pro
                85                  90                  95

Leu Ile Thr Phe Gly Ala Gly Thr Lys Leu Glu Leu Lys Arg Ala Asp
            100                 105                 110

-continued

```
Ala Ala Pro Thr Val Ser Ile Phe Pro Pro Ser Ser Glu Gln
        115                 120                 125

<210> SEQ ID NO 11
<211> LENGTH: 7
<212> TYPE: PRT
<213> ORGANISM: Artificial sequence
<220> FEATURE:
<223> OTHER INFORMATION: Synthetic antibody

<400> SEQUENCE: 11

Ser Ser Val Ser Ser Ser Tyr
1               5

<210> SEQ ID NO 12
<211> LENGTH: 21
<212> TYPE: DNA
<213> ORGANISM: Artificial sequence
<220> FEATURE:
<223> OTHER INFORMATION: Synthetic antibody

<400> SEQUENCE: 12
tcaagtgtaa gttccagtta c                                              21

<210> SEQ ID NO 13
<211> LENGTH: 3
<212> TYPE: PRT
<213> ORGANISM: Artificial sequence
<220> FEATURE:
<223> OTHER INFORMATION: Synthetic antibody

<400> SEQUENCE: 13

Ser Thr Ser
1

<210> SEQ ID NO 14
<211> LENGTH: 9
<212> TYPE: DNA
<213> ORGANISM: Artificial sequence
<220> FEATURE:
<223> OTHER INFORMATION: Synthetic antibody

<400> SEQUENCE: 14 agcacatcc                                                            9

<210> SEQ ID NO 15
<211> LENGTH: 10
<212> TYPE: PRT
<213> ORGANISM: Artificial sequence
<220> FEATURE:
<223> OTHER INFORMATION: Synthetic antibody

<400> SEQUENCE: 15

Gln Gln Tyr Ser Gly Tyr Pro Leu Ile Thr
1               5                   10

<210> SEQ ID NO 16
<211> LENGTH: 30
<212> TYPE: DNA
<213> ORGANISM: Artificial sequence
<220> FEATURE:
<223> OTHER INFORMATION: Synthetic antibody

<400> SEQUENCE: 16
cagcagtaca gtggttaccc actcatcacg                                     30
```

<210> SEQ ID NO 17
<211> LENGTH: 363
<212> TYPE: DNA
<213> ORGANISM: Artificial sequence
<220> FEATURE:
<223> OTHER INFORMATION: Synthetic antibody

<400> SEQUENCE: 17
aggtgaagct gcagcagtca ggacctgagc tggtgaagcc tggggcttca gtgaagatat        60
cctgtaaggc ttctggatac acgttcactg actactacat gaactgggtg aagcagagcc       120
atggaaagag ccttgagtgg attggagata ttaatcctaa caatgatggt actacctact       180
acaaccagaa gttcaagggc aaggccacat tgactgtaga caagtcctcc agcacagcct       240
acatggagct ccgcagcctg acatctgagg actctgcagt ctattactgt gcaagatccc       300
tctacggtag tagctactac tttgactact ggggccaagg caccactctc acagtctcct       360
cag                                                                     363

<210> SEQ ID NO 18
<211> LENGTH: 120
<212> TYPE: PRT
<213> ORGANISM: Artificial sequence
<220> FEATURE:
<223> OTHER INFORMATION: Synthetic antibody

<400> SEQUENCE: 18

Val Lys Leu Gln Gln Ser Gly Pro Glu Leu Val Lys Pro Gly Ala Ser
1               5                   10                  15

Val Lys Ile Ser Cys Lys Ala Ser Gly Tyr Thr Phe Thr Asp Tyr Tyr
                20                  25                  30

Met Asn Trp Val Lys Gln Ser His Gly Lys Ser Leu Glu Trp Ile Gly
            35                  40                  45

Asp Ile Asn Pro Asn Asn Asp Gly Thr Thr Tyr Tyr Asn Gln Lys Phe
        50                  55                  60

Lys Gly Lys Ala Thr Leu Thr Val Asp Lys Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Arg Ser Leu Tyr Gly Ser Ser Tyr Tyr Phe Asp Tyr Trp Gly Gln
            100                 105                 110

Gly Thr Thr Leu Thr Val Ser Ser
        115                 120

<210> SEQ ID NO 19
<211> LENGTH: 8
<212> TYPE: PRT
<213> ORGANISM: Artificial sequence
<220> FEATURE:
<223> OTHER INFORMATION: Synthetic antibody

<400> SEQUENCE: 19

Gly Tyr Thr Phe Thr Asp Tyr Tyr
1               5

<210> SEQ ID NO 20
<211> LENGTH: 24
<212> TYPE: DNA
<213> ORGANISM: Artificial sequence
<220> FEATURE:
<223> OTHER INFORMATION: Synthetic antibody

<400> SEQUENCE: 20
ggatacacgt tcactgacta ctac                                                    24

<210> SEQ ID NO 21
<211> LENGTH: 8
<212> TYPE: PRT
<213> ORGANISM: Artificial sequence
<220> FEATURE:
<223> OTHER INFORMATION: Synthetic antibody

<400> SEQUENCE: 21

Ile Asn Pro Asn Asn Asp Gly Thr
1               5

<210> SEQ ID NO 22
<211> LENGTH: 24
<212> TYPE: DNA
<213> ORGANISM: Artificial sequence
<220> FEATURE:
<223> OTHER INFORMATION: Synthetic antibody

<400> SEQUENCE: 22
attaatccta acaatgatgg tact                                                    24

<210> SEQ ID NO 23
<211> LENGTH: 13
<212> TYPE: PRT
<213> ORGANISM: Artificial sequence
<220> FEATURE:
<223> OTHER INFORMATION: Synthetic antibody

<400> SEQUENCE: 23

Ala Arg Ser Leu Tyr Gly Ser Ser Tyr Tyr Phe Asp Tyr
1               5                   10

<210> SEQ ID NO 24
<211> LENGTH: 39
<212> TYPE: DNA
<213> ORGANISM: Artificial sequence
<220> FEATURE:
<223> OTHER INFORMATION: Synthetic antibody

<400> SEQUENCE: 24
gcaagatccc tctacggtag tagctactac tttgactac                                    39

<210> SEQ ID NO 25
<211> LENGTH: 334
<212> TYPE: DNA
<213> ORGANISM: Artificial sequence
<220> FEATURE:
<223> OTHER INFORMATION: Synthetic antibody

<400> SEQUENCE: 25
gatattgtga tgacacagtc tcctgcttcc ttagctgtat ctctggggca gagggccacc      60
atctcataca gggccagcaa aagtgtcagt acatctggct atagttatat gcactggaac     120
caacagaaac caggacagcc acccagactc ctcatctatc ttgtatccaa cctagaatct     180
gggatcccag ccaggtttag tggcagtggg tctgggacag acttcaccct caacatccat     240
cctgtggagg aggaggatgc tgcaacctat tactgtcagc aaagtaatga ggaccgtgg      300 acgttcggtg gaggcaccaa gctggaaatc aaac                                 334

<210> SEQ ID NO 26
<211> LENGTH: 111

-continued

```
<212> TYPE: PRT
<213> ORGANISM: Artificial sequence
<220> FEATURE:
<223> OTHER INFORMATION: Synthetic antibody

<400> SEQUENCE: 26

Asp Ile Val Met Thr Gln Ser Pro Ala Ser Leu Ala Val Ser Leu Gly
1               5                   10                  15

Gln Arg Ala Thr Ile Ser Tyr Arg Ala Ser Lys Ser Val Ser Thr Ser
            20                  25                  30

Gly Tyr Ser Tyr Met His Trp Asn Gln Gln Lys Pro Gly Gln Pro Pro
        35                  40                  45

Arg Leu Leu Ile Tyr Leu Val Ser Asn Leu Glu Ser Gly Ile Pro Ala
    50                  55                  60

Arg Phe Ser Gly Ser Gly Ser Gly Thr Asp Phe Thr Leu Asn Ile His
65              70                  75                  80

Pro Val Glu Glu Glu Asp Ala Ala Thr Tyr Tyr Cys Gln Gln Ser Asn
                85                  90                  95

Glu Asp Pro Trp Thr Phe Gly Gly Gly Thr Lys Leu Glu Ile Lys
            100                 105                 110

<210> SEQ ID NO 27
<211> LENGTH: 10
<212> TYPE: PRT
<213> ORGANISM: Artificial sequence
<220> FEATURE:
<223> OTHER INFORMATION: Synthetic antibody

<400> SEQUENCE: 27

Lys Ser Val Ser Thr Ser Gly Tyr Ser Tyr
1               5                   10

<210> SEQ ID NO 28
<211> LENGTH: 30
<212> TYPE: DNA
<213> ORGANISM: Artificial sequence
<220> FEATURE:
<223> OTHER INFORMATION: Synthetic antibody

<400> SEQUENCE: 28
aaaagtgtca gtacatctgg ctatagttat                                    30

<210> SEQ ID NO 29
<211> LENGTH: 3
<212> TYPE: PRT
<213> ORGANISM: Artificial sequence
<220> FEATURE:
<223> OTHER INFORMATION: Synthetic antibody

<400> SEQUENCE: 29

Leu Val Ser
1

<210> SEQ ID NO 30
<211> LENGTH: 9
<212> TYPE: DNA
<213> ORGANISM: Artificial sequence
<220> FEATURE:
<223> OTHER INFORMATION: Synthetic antibody

<400> SEQUENCE: 30 cttgtatcc                                                            9
```

-continued

<210> SEQ ID NO 31
<211> LENGTH: 9
<212> TYPE: PRT
<213> ORGANISM: Artificial sequence
<220> FEATURE:
<223> OTHER INFORMATION: Synthetic antibody

<400> SEQUENCE: 31

Gln Gln Ser Asn Glu Asp Pro Trp Thr
1               5

<210> SEQ ID NO 32
<211> LENGTH: 27
<212> TYPE: DNA
<213> ORGANISM: Artificial sequence
<220> FEATURE:
<223> OTHER INFORMATION: Synthetic antibody

<400> SEQUENCE: 32
cagcaaagta atgaggaccc gtggacg                                              27

<210> SEQ ID NO 33
<211> LENGTH: 354
<212> TYPE: DNA
<213> ORGANISM: Artificial sequence
<220> FEATURE:
<223> OTHER INFORMATION: Synthetic antibody

<400> SEQUENCE: 33
aggtgcagct gcaggagtct gggggaggct tagtgaagcc tggagggtcc ctgaaactct        60
cctgtgcagc ctctggattc actttcagtg actatggaat gcactgggtt cgtcaggctc       120
cagagaaggg gctggagtgg gttgcataca ttagtagtgg cagtaattcc atctactatg       180
cagacacagt gacgggccga ttcaccatct ccagagacaa tgccaagaac accctgttcc       240
tgcaaatgac cagtctgagg tctgaggaca cggccatgta ttactgtgcc tcgaataatg       300
gttacttcta ctttgactac tggggccaag gcaccactct cacagtctcc tcag            354

<210> SEQ ID NO 34
<211> LENGTH: 117
<212> TYPE: PRT
<213> ORGANISM: Artificial sequence
<220> FEATURE:
<223> OTHER INFORMATION: Synthetic antibody

<400> SEQUENCE: 34

Val Gln Leu Gln Glu Ser Gly Gly Gly Leu Val Lys Pro Gly Gly Ser
1               5                   10                  15

Leu Lys Leu Ser Cys Ala Ala Ser Gly Phe Thr Phe Ser Asp Tyr Gly
                20                  25                  30

Met His Trp Val Arg Gln Ala Pro Glu Lys Gly Leu Glu Trp Val Ala
            35                  40                  45

Tyr Ile Ser Ser Gly Ser Asn Ser Ile Tyr Tyr Ala Asp Thr Val Thr
        50                  55                  60

Gly Arg Phe Thr Ile Ser Arg Asp Asn Ala Lys Asn Thr Leu Phe Leu
65                  70                  75                  80

Gln Met Thr Ser Leu Arg Ser Glu Asp Thr Ala Met Tyr Tyr Cys Ala
                85                  90                  95

Ser Asn Asn Gly Tyr Phe Tyr Phe Asp Tyr Trp Gly Gln Gly Thr Thr
            100                 105                 110

Leu Thr Val Ser Ser
            115

```
<210> SEQ ID NO 35
<211> LENGTH: 8
<212> TYPE: PRT
<213> ORGANISM: Artificial sequence
<220> FEATURE:
<223> OTHER INFORMATION: Synthetic antibody

<400> SEQUENCE: 35

Gly Phe Thr Phe Ser Thr Tyr Gly
1               5

<210> SEQ ID NO 36
<211> LENGTH: 24
<212> TYPE: DNA
<213> ORGANISM: Artificial sequence
<220> FEATURE:
<223> OTHER INFORMATION: Synthetic antibody

<400> SEQUENCE: 36
ggattcactt tcagtgacta tgga                                    24

<210> SEQ ID NO 37
<211> LENGTH: 8
<212> TYPE: PRT
<213> ORGANISM: Artificial sequence
<220> FEATURE:
<223> OTHER INFORMATION: Synthetic antibody

<400> SEQUENCE: 37

Ile Ser Ser Gly Ser Asn Ser Ile
1               5

<210> SEQ ID NO 38
<211> LENGTH: 24
<212> TYPE: DNA
<213> ORGANISM: Artificial sequence
<220> FEATURE:
<223> OTHER INFORMATION: Synthetic antibody

<400> SEQUENCE: 38
attagtagtg gcagtaattc catc                                    24

<210> SEQ ID NO 39
<211> LENGTH: 11
<212> TYPE: PRT
<213> ORGANISM: Artificial sequence
<220> FEATURE:
<223> OTHER INFORMATION: Synthetic antibody

<400> SEQUENCE: 39

Ala Ser Asn Asn Gly Tyr Phe Tyr Phe Asp Tyr
1               5                   10

<210> SEQ ID NO 40
<211> LENGTH: 33
<212> TYPE: DNA
<213> ORGANISM: Artificial sequence
<220> FEATURE:
<223> OTHER INFORMATION: Synthetic antibody

<400> SEQUENCE: 40
gcctcgaata atggttactt ctactttgac tac                          33

<210> SEQ ID NO 41
<211> LENGTH: 316
```

<212> TYPE: DNA
<213> ORGANISM: Artificial sequence
<220> FEATURE:
<223> OTHER INFORMATION: Synthetic antibody

<400> SEQUENCE: 41
attgtgatca cccagtctcc agcaatcctg tctgcatctc caggggagaa ggtcacaatg     60
acttgcaggg ccagctcaag tgtaagttac atgcactggt accagcagaa gccaggatcc    120
tcccccaaac cctggattta tgccacatcc aacctggctt ctggagtccc tgctcgcttc    180
agtggcagtg gtctgggac ctcttactct ctcacagtca gcagagtgga ggctgaagat     240
gctgccactt attactgcca gcagtggagt agtgacccat tcacgttcgg ctcggggaca    300
aagttggaaa taaaac                                                     316

<210> SEQ ID NO 42
<211> LENGTH: 105
<212> TYPE: PRT
<213> ORGANISM: Artificial sequence
<220> FEATURE:
<223> OTHER INFORMATION: Synthetic antibody

<400> SEQUENCE: 42

Ile Val Ile Thr Gln Ser Pro Ala Ile Leu Ser Ala Ser Pro Gly Glu
1                   5                   10                  15

Lys Val Thr Met Thr Cys Arg Ala Ser Ser Ser Val Ser Tyr Met His
                20                  25                  30

Trp Tyr Gln Gln Lys Pro Gly Ser Ser Pro Lys Pro Trp Ile Tyr Ala
            35                  40                  45

Thr Ser Asn Leu Ala Ser Gly Val Pro Ala Arg Phe Ser Gly Ser Gly
        50                  55                  60

Ser Gly Thr Ser Tyr Ser Leu Thr Val Ser Arg Val Glu Ala Glu Asp
65                  70                  75                  80

Ala Ala Thr Tyr Tyr Cys Gln Gln Trp Ser Ser Asp Pro Phe Thr Phe
                85                  90                  95

Gly Ser Gly Thr Lys Leu Glu Ile Lys
            100                 105

<210> SEQ ID NO 43
<211> LENGTH: 5
<212> TYPE: PRT
<213> ORGANISM: Artificial sequence
<220> FEATURE:
<223> OTHER INFORMATION: Synthetic antibody

<400> SEQUENCE: 43

Ser Ser Val Ser Tyr
1               5

<210> SEQ ID NO 44
<211> LENGTH: 15
<212> TYPE: DNA
<213> ORGANISM: Artificial sequence
<220> FEATURE:
<223> OTHER INFORMATION: Synthetic antibody

<400> SEQUENCE: 44
tcaagtgtaa gttac                                                       15

<210> SEQ ID NO 45
<211> LENGTH: 3
<212> TYPE: PRT

```
<213> ORGANISM: Artificial sequence
<220> FEATURE:
<223> OTHER INFORMATION: Synthetic antibody

<400> SEQUENCE: 45

Ala Thr Ser
1

<210> SEQ ID NO 46
<211> LENGTH: 9
<212> TYPE: DNA
<213> ORGANISM: Artificial sequence
<220> FEATURE:
<223> OTHER INFORMATION: Synthetic antibody

<400> SEQUENCE: 46 gccacatcc                                                                    9

<210> SEQ ID NO 47
<211> LENGTH: 9
<212> TYPE: PRT
<213> ORGANISM: Artificial sequence
<220> FEATURE:
<223> OTHER INFORMATION: Synthetic antibody

<400> SEQUENCE: 47

Gln Gln Trp Ser Ser Asp Pro Phe Thr
1               5

<210> SEQ ID NO 48
<211> LENGTH: 27
<212> TYPE: DNA
<213> ORGANISM: Artificial sequence
<220> FEATURE:
<223> OTHER INFORMATION: Synthetic antibody

<400> SEQUENCE: 48
cagcagtgga gtagtgaccc attcacg                                                27

<210> SEQ ID NO 49
<211> LENGTH: 363
<212> TYPE: DNA
<213> ORGANISM: Artificial sequence
<220> FEATURE:
<223> OTHER INFORMATION: Synthetic antibody

<400> SEQUENCE: 49
aggtgaaact gcagcagtca ggacctgagc tggtgaagcc tggggcttca gtgaagatat     60
cctgtaaggc ttctggatac acgttcactg actactacat gaactgggtg aaggagagcc    120
atggaaagag ccttgagtgg attggagata ttaatcctaa caatggtggt tctacctact    180
acaaccagaa gttcaagggc aaggccacat tgactgtaga gaagtcctcc agcacagcct    240
tcatggagct ccgcagcctg acatctgagg actctgcagt ctattactgt gcaagatccc    300
tctacggtag tacctactac tttgactact ggggccaagg cacccctctc acagtctcct    360
cag                                                                  363

<210> SEQ ID NO 50
<211> LENGTH: 120
<212> TYPE: PRT
<213> ORGANISM: Artificial sequence
<220> FEATURE:
<223> OTHER INFORMATION: Synthetic antibody

<400> SEQUENCE: 50
```

```
Val Lys Leu Gln Gln Ser Gly Pro Glu Leu Val Lys Pro Gly Ala Ser
1               5                   10                  15

Val Lys Ile Ser Cys Lys Ala Ser Gly Tyr Thr Phe Thr Asp Tyr Tyr
            20                  25                  30

Met Asn Trp Val Lys Glu Ser His Gly Lys Ser Leu Glu Trp Ile Gly
        35                  40                  45

Asp Ile Asn Pro Asn Asn Gly Gly Ser Thr Tyr Tyr Asn Gln Lys Phe
    50                  55                  60

Lys Gly Lys Ala Thr Leu Thr Val Glu Lys Ser Ser Ser Thr Ala Phe
65                  70                  75                  80

Met Glu Leu Arg Ser Leu Thr Ser Glu Asp Ser Ala Val Tyr Tyr Cys
                85                  90                  95

Ala Arg Ser Leu Tyr Gly Ser Thr Tyr Tyr Phe Asp Tyr Trp Gly Gln
                100                 105                 110

Gly Thr Pro Leu Thr Val Ser Ser
        115                 120
```

```
<210> SEQ ID NO 51
<211> LENGTH: 8
<212> TYPE: PRT
<213> ORGANISM: Artificial sequence
<220> FEATURE:
<223> OTHER INFORMATION: Synthetic antibody

<400> SEQUENCE: 51

Gly Tyr Thr Phe Thr Asp Tyr Tyr
1               5
```

```
<210> SEQ ID NO 52
<211> LENGTH: 24
<212> TYPE: DNA
<213> ORGANISM: Artificial sequence
<220> FEATURE:
<223> OTHER INFORMATION: Synthetic antibody

<400> SEQUENCE: 52
ggatacacgt tcactgacta ctac                                              24
```

```
<210> SEQ ID NO 53
<211> LENGTH: 8
<212> TYPE: PRT
<213> ORGANISM: Artificial sequence
<220> FEATURE:
<223> OTHER INFORMATION: Synthetic antibody

<400> SEQUENCE: 53

Ile Asn Pro Asn Asn Gly Gly Ser
1               5
```

```
<210> SEQ ID NO 54
<211> LENGTH: 24
<212> TYPE: DNA
<213> ORGANISM: Artificial sequence
<220> FEATURE:
<223> OTHER INFORMATION: Synthetic antibody

<400> SEQUENCE: 54
attaatccta acaatggtgg ttct                                              24
```

```
<210> SEQ ID NO 55
<211> LENGTH: 13
<212> TYPE: PRT
```

```
<213> ORGANISM: Artificial sequence
<220> FEATURE:
<223> OTHER INFORMATION: Synthetic antibody

<400> SEQUENCE: 55

Ala Arg Ser Leu Tyr Gly Ser Thr Tyr Tyr Phe Asp Tyr
1               5                   10

<210> SEQ ID NO 56
<211> LENGTH: 39
<212> TYPE: DNA
<213> ORGANISM: Artificial sequence
<220> FEATURE:
<223> OTHER INFORMATION: Synthetic antibody

<400> SEQUENCE: 56
gcaagatccc tctacggtag tacctactac tttgactac                              39

<210> SEQ ID NO 57
<211> LENGTH: 334
<212> TYPE: DNA
<213> ORGANISM: Artificial sequence
<220> FEATURE:
<223> OTHER INFORMATION: Synthetic antibody

<400> SEQUENCE: 57
gatattgtgc tgacccagtc tccagcttct ttggctgtgt ctctagggca gagggccacc    60
atctcctgca aggccagcca aagtgttgat tatgatggtg atagttatat gaactggtac   120
caacagaagc caggacagcc acccaaactc ctcatctatg ctgcatccaa tctagaatct   180
gggatcccag ccaggtttag tggcagtggg tctgggacag acttcactct caacatccat   240
cctgtggagg aggaggatgc tggaacctat tactgtcagc aaagtaatga cgatccgtgg   300
acgttcggtg gaggcaccaa gctggaaatc aaac                              334

<210> SEQ ID NO 58
<211> LENGTH: 111
<212> TYPE: PRT
<213> ORGANISM: Artificial sequence
<220> FEATURE:
<223> OTHER INFORMATION: Synthetic antibody

<400> SEQUENCE: 58

Asp Ile Val Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Met Asn Trp Tyr Gln Gln Lys Pro Gly Gln Pro Pro
        35                  40                  45

Lys Leu Leu Ile Tyr Ala Ala Ser Asn Leu Glu Ser Gly Ile Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Gly Thr Tyr Tyr Cys Gln Gln Ser Asn
                85                  90                  95

Asp Asp Pro Trp Thr Phe Gly Gly Gly Thr Lys Leu Glu Ile Lys
            100                 105                 110

<210> SEQ ID NO 59
<211> LENGTH: 10
<212> TYPE: PRT
<213> ORGANISM: Artificial sequence
```

-continued

```
<220> FEATURE:
<223> OTHER INFORMATION: Synthetic antibody

<400> SEQUENCE: 59

Gln Ser Val Asp Tyr Asp Gly Asp Ser Tyr
1               5                   10

<210> SEQ ID NO 60
<211> LENGTH: 30
<212> TYPE: DNA
<213> ORGANISM: Artificial sequence
<220> FEATURE:
<223> OTHER INFORMATION: Synthetic antibody

<400> SEQUENCE: 60
caaagtgttg attatgatgg tgatagttat                                    30

<210> SEQ ID NO 61
<211> LENGTH: 3
<212> TYPE: PRT
<213> ORGANISM: Artificial sequence
<220> FEATURE:
<223> OTHER INFORMATION: Synthetic antibody

<400> SEQUENCE: 61

Ala Ala Ser
1

<210> SEQ ID NO 62
<211> LENGTH: 9
<212> TYPE: DNA
<213> ORGANISM: Artificial sequence
<220> FEATURE:
<223> OTHER INFORMATION: Synthetic antibody

<400> SEQUENCE: 62 gctgcatcc                                                            9

<210> SEQ ID NO 63
<211> LENGTH: 9
<212> TYPE: PRT
<213> ORGANISM: Artificial sequence
<220> FEATURE:
<223> OTHER INFORMATION: Synthetic antibody

<400> SEQUENCE: 63

Gln Gln Ser Asn Asp Asp Pro Trp Thr
1               5

<210> SEQ ID NO 64
<211> LENGTH: 27
<212> TYPE: DNA
<213> ORGANISM: Artificial sequence
<220> FEATURE:
<223> OTHER INFORMATION: Synthetic antibody

<400> SEQUENCE: 64
cagcaaagta atgacgatcc gtggacg                                        27
```

HUMAN 4-1BB AGONIST ANTIBODIES AND METHODS OF USE THEREOF

This application is a national phase application under 35 U.S.C. § 371 of International Application No. PCT/US2021/018276, filed Feb. 17, 2021, which claims the benefit of U.S. Provisional Patent Application No. 62/977,658, filed Feb. 17, 2020, each of which is incorporated herein by reference in its entirety.

INCORPORATION OF SEQUENCE LISTING

The sequence listing that is contained in the file named "UTSC.P1467US-ST25.txt", which is 23,398 bytes (as measured in Microsoft Windows®) and was created on Jan. 30, 2026, is filed herewith by electronic submission and is incorporated by reference herein.

BACKGROUND

1. Field

The present invention relates generally to the field of molecular biology. More particularly, it concerns tumor necrosis factor superfamily receptor (TNFSFR; 4-1 BB; CD137) agonist antibodies.

2. Description of Related Art 4-1BB (CD137), a member of the TNF receptor superfamily, is an activation-induced T-cell costimulatory molecule (Vinay and Kwon, 2012). Signaling via 4-1BB upregulates survival genes, enhances cell division, induces cytokine production, and prevents activation-induced cell death in T cells. The importance of the 4-1BB pathway has been underscored in a number of diseases, including cancer. Growing evidence indicates that anti-4-1BB monoclonal antibodies possess strong antitumor properties, which in turn are the result of their powerful CD8$^+$ T-cell activating, IFN-γ producing, and cytolytic marker-inducing capabilities. In addition, combination therapy of anti-4-1BB with other anticancer agents, such as radiation, has robust tumor-regressing abilities against nonimmunogenic or poorly immunogenic tumors. Furthermore, the adoptive transfer of ex vivo anti-4-1BB-activated CD8$^+$ T cells from previously tumor-treated animals efficiently inhibits progression of tumors in recipient mice that have been inoculated with fresh tumors. In addition, targeting of tumors with variants of 4-1BBL directed against 4-1BB also have potent antitumor effects. However, there is an unmet need for improved human 4-1BB antibodies.

SUMMARY

In a first embodiment, the present disclosure provides isolated monoclonal antibodies, wherein the antibody specifically binds to 4-1BB and comprises: (a) a first $V_H$ CDR is identical to SEQ ID NO: 3; (b) a second $V_H$ CDR is identical to SEQ ID NO: 5; (c) a third $V_H$ CDR is identical to SEQ ID NO: 7; (d) a first $V_L$ CDR is identical to SEQ ID NO: 11; (e) a second $V_L$ CDR is identical to SEQ ID NO: 13; and (f) a third $V_L$ CDR is identical to SEQ ID NO: 15; or (a) a first $V_H$ CDR is identical to SEQ ID NO: 19; (b) a second $V_H$ CDR is identical to SEQ ID NO: 21; (c) a third $V_H$ CDR is identical to SEQ ID NO: 23; (d) a first $V_L$ CDR is identical to SEQ ID NO: 27; (e) a second $V_L$ CDR is identical to SEQ ID NO: 29; and (f) a third $V_L$ CDR is identical to SEQ ID NO: 31; or (a) a first $V_H$ CDR is identical to SEQ ID NO: 35; (b) a second $V_H$ CDR is identical to SEQ ID NO: 37; (c) a third $V_H$ CDR is identical to SEQ ID NO: 39; (d) a first $V_L$ CDR is identical to SEQ ID NO: 43; (e) a second $V_L$ CDR is identical to SEQ ID NO: 45; and (f) a third $V_L$ CDR is identical to SEQ ID NO: 47; or (a) a first $V_H$ CDR is identical to SEQ ID NO: 51; (b) a second $V_H$ CDR is identical to SEQ ID NO: 53; (c) a third $V_H$ CDR is identical to SEQ ID NO: 55; (d) a first $V_L$ CDR is identical to SEQ ID NO: 59; (e) a second $V_L$ CDR is identical to SEQ ID NO: 61; and (f) a third $V_L$ CDR is identical to SEQ ID NO: 63.

In some aspects, the antibody comprises a $V_H$ domain at least about 80% identical, such as 85%, 90%, 91%, 92%, 93%, 94%, 95%, 96%, 97%, 98%, 99%, or 100% identical, to the $V_H$ domain of clone 54 (SEQ ID NO: 2) and a $V_L$ domain at least about 80% identical, such as 85%, 90%, 91%, 92%, 93%, 94%, 95%, 96%, 97%, 98%, 99%, or 100% identical, to the $V_L$ domain of clone 54 (SEQ ID NO: 10). In particular aspects, the antibody comprises a $V_H$ domain identical to the $V_H$ domain of clone 54 (SEQ ID NO: 2) and a $V_L$ domain identical to the $V_L$ domain of clone 54 (SEQ ID NO: 10).

In certain aspects, the antibody comprises a $V_H$ domain at least about 80% identical, such as 85%, 90%, 91%, 92%, 93%, 94%, 95%, 96%, 97%, 98%, 99%, or 100% identical, to the $V_H$ domain of clone 135B (SEQ ID NO: 18) and a $V_L$ domain at least about 80% identical, such as 85%, 90%, 91%, 92%, 93%, 94%, 95%, 96%, 97%, 98%, 99%, or 100% identical, to the $V_L$ domain of clone 135B (SEQ ID NO: 26). In specific aspects, the antibody comprises a $V_H$ domain identical to the $V_H$ domain of clone 135B (SEQ ID NO: 18) and a $V_L$ domain identical to the $V_L$ domain of clone 135B (SEQ ID NO: 26).

In some aspects, the antibody comprises a $V_H$ domain at least about 80% identical, such as 85%, 90%, 91%, 92%, 93%, 94%, 95%, 96%, 97%, 98%, 99%, or 100% identical, to the $V_H$ domain of clone 138 (SEQ ID NO: 34) and a $V_L$ domain at least about 80% identical, such as 85%, 90%, 91%, 92%, 93%, 94%, 95%, 96%, 97%, 98%, 99%, or 100% identical, to the $V_L$ domain of clone 138 (SEQ ID NO: 42). In particular aspects, the antibody comprises a $V_H$ domain identical to the $V_H$ domain of clone 138 (SEQ ID NO: 34) and a $V_L$ domain identical to the $V_L$ domain of clone 138 (SEQ ID NO: 42).

In some aspects, the antibody comprises a $V_H$ domain at least about 80% identical, such as 85%, 90%, 91%, 92%, 93%, 94%, 95%, 96%, 97%, 98%, 99%, or 100% identical, to the $V_H$ domain of clone 49A (SEQ ID NO: 50) and a $V_L$ domain at least about 80% identical, such as 85%, 90%, 91%, 92%, 93%, 94%, 95%, 96%, 97%, 98%, 99%, or 100% identical, to the $V_L$ domain of clone 49A (SEQ ID NO: 58). In specific aspects, the antibody comprises a $V_H$ domain identical to the $V_H$ domain of clone 49A (SEQ ID NO: 50) and a $V_L$ domain identical to the $V_L$ domain of clone 49A (SEQ ID NO: 58).

In certain aspects, the antibody is recombinant. In some aspects, the antibody is an IgG, IgM, IgA or an antigen binding fragment thereof. In certain aspects, the antibody is a Fab', a F(ab')2, a F(ab')3, a monovalent scFv, a bivalent scFv, or a single domain antibody. In specific aspects, the antibody is a human, humanized antibody or de-immunized antibody. In further aspects, the antibody is conjugated to an imaging agent, a chemotherapeutic agent, a toxin or a radionuclide.

A further embodiment provides a composition comprising an antibody of the present embodiments in a pharmaceutically acceptable carrier. Also provided herein is an isolated polynucleotide molecule comprising a nucleic acid sequence encoding an antibody of the present embodiments.

Another embodiment provides a recombinant polypeptide comprising an antibody V$_H$ domain comprising CDRs 1-3 of the V$_H$ domain of clone 54 (SEQ ID NOs: 3, 5, and 7), CDRs 1-3 of the V$_H$ domain of clone 135B (SEQ ID NOs: 19, 21, and 23), CDRs 1-3 of the V$_H$ domain of clone 138 (SEQ ID NOs: 35, 37, and 39), or CDRs 1-3 of the V$_H$ domain of clone 49A (SEQ ID NOs: 51, 53, and 55).

Further embodiments provide recombinant polypeptides comprising an antibody V$_L$ domain comprising CDRs 1-3 of the V$_L$ domain of 54 (SEQ ID NOs: 11, 13, and 15), CDRs 1-3 of the V$_L$ domain of 135B (SEQ ID NOs: 27, 29, and 31), CDRs 1-3 of the V$_L$ domain of 138 (SEQ ID NOs: 43, 45, and 47), or CDRs 1-3 of the V$_L$ domain of 49A (SEQ ID NOs: 59, 61, and 63).

In yet a further embodiment, there is provided a recombinant polypeptide comprising an antibody V$_H$ domain comprising CDRs 1-3 of the V$_H$ domain of clone 54 (SEQ ID NOs: 3, 5, and 7) and an antibody V$_L$ domain comprising CDRs 1-3 of the V$_L$ domain of 54 (SEQ ID NOs: 11, 13, and 15); an antibody V$_H$ domain comprising CDRs 1-3 of the V$_H$ domain of clone 135B (SEQ ID NOs: 19, 21, and 23) and an antibody V$_L$ domain comprising CDRs 1-3 of the V$_L$ domain of 135B (SEQ ID NOs: 27, 29, and 31); an antibody V$_H$ domain comprising CDRs 1-3 of the V$_H$ domain of clone 138 (SEQ ID NOs: 35, 37, and 39) and an antibody V$_L$ domain comprising CDRs 1-3 of the V$_L$ domain of 138 (SEQ ID NOs: 43, 45, and 47); or an antibody V$_H$ domain comprising CDRs 1-3 of the V$_H$ domain of clone 49A (SEQ ID NOs: 51, 53, and 55) and an antibody V$_L$ domain comprising CDRs 1-3 of the V$_L$ domain of 49A (SEQ ID NOs: 59, 61, and 63).

Further embodiments provide isolated polynucleotide molecules comprising a nucleic acid sequence encoding a polypeptide of the present embodiments. Also provided herein is a host cell comprising one or more polynucleotide molecule(s) encoding an antibody of the present embodiments or a recombinant polypeptide of the present embodiments. In some aspects, the host cell is a mammalian cell, a yeast cell, a bacterial cell, a ciliate cell or an insect cell.

Another embodiment provides a method of manufacturing an antibody comprising: (a) expressing one or more polynucleotide molecule(s) encoding a V$_L$ and V$_H$ chain of an antibody of the present embodiments in a cell; and (b) purifying the antibody from the cell.

A further embodiment provides a method for treating a subject having a cancer comprising administering an effective amount of an antibody of the present embodiments to the subject.

In some aspects, the cancer is a breast cancer, lung cancer, head & neck cancer, prostate cancer, esophageal cancer, tracheal cancer, skin cancer brain cancer, liver cancer, bladder cancer, stomach cancer, pancreatic cancer, ovarian cancer, uterine cancer, cervical cancer, testicular cancer, colon cancer, rectal cancer or skin cancer.

In specific aspects, the antibody is in a pharmaceutically acceptable composition. In some aspects, the antibody is administered systemically. In some aspects, the antibody is administered intravenously, intradermally, intratumorally, intramuscularly, intraperitoneally, subcutaneously, or locally.

In additional aspects, the method further comprises administering at least a second anticancer therapy to the subject. In some aspects, the second anticancer therapy is a surgical therapy, chemotherapy, radiation therapy, cryotherapy, hormonal therapy, immunotherapy or cytokine therapy. In certain aspects, the second anticancer therapy comprises an adoptive T-cell therapy. In some aspects, the second anticancer therapy comprises an immunotherapy. In particular aspects, the immunotherapy is an immune checkpoint inhibitor, such as an anti-CTLA-4 antibody, an anti-PD-L1 antibody, and/or an anti-PD1 antibody. In specific aspects, the immune checkpoint inhibitor is a human programmed cell death 1 (PD-1) binding antagonist, a PDL1 binding antagonist or a PDL2 binding antagonist. In some aspects, the PD-1 binding antagonist is a monoclonal antibody or antigen binding fragment thereof. In certain aspects, the PD-1 binding antagonist is nivolumab, pembrolizumab, CT-011, BMS 936559, MPDL328OA or AMP-224.

Other objects, features and advantages of the present invention will become apparent from the following detailed description. It should be understood, however, that the detailed description and the specific examples, while indicating certain embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

(FIG. 1A) Shown are ELISA results for initial post-fusion antibody supernatants against recombinant human 4-1BB. (FIG. 1B) Titration curves of 4-1BB monoclonal antibody clones.

DESCRIPTION OF ILLUSTRATIVE EMBODIMENTS

Figure 1A:
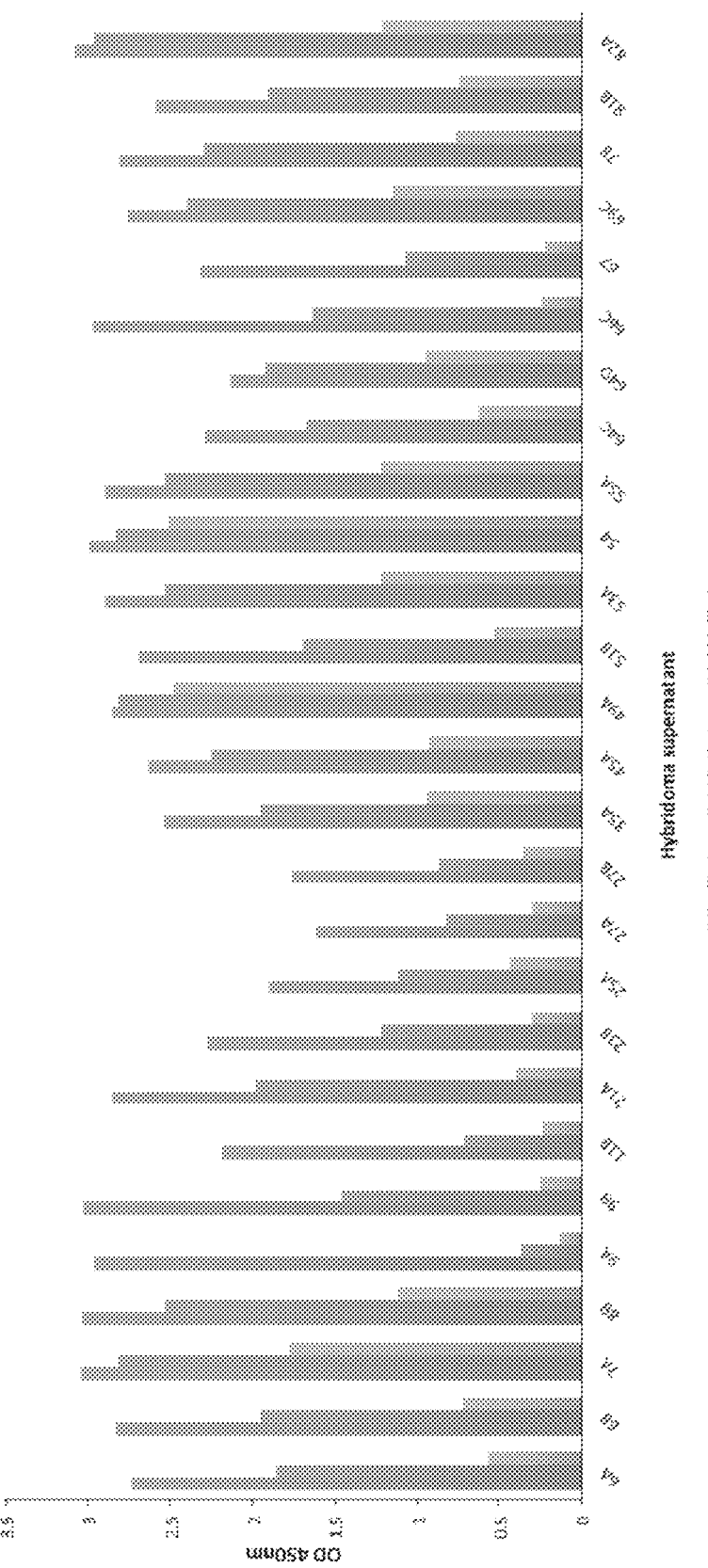
FIGS. 1A-1B: Multiple high-affinity anti-human 4-1BB antibodies were generated.

The Tumor Necrosis Factor Superfamily Receptor (TNFSFR), also known as 4-1BB and CD137, co-stimulates the activation of T cells, NK cells, and myeloid cells including antigen-presenting dendritic cells. On CD8 T cells, 4-1BB activation increases their proliferation, cytotoxicity, cytokine production, mitochondrial mass, and viability. Thus, in the present studies 4-1BB agonist anti-bodies were generated. Mice were immunized with alter-nating cellular and recombinant protein-based vaccines in order to generate antibodies targeting human 4-1BB. Among many lead candidates, the clone 54 4-1BB antibody was selected which was sequenced and expressed in a variety of mouse and human isotypes. The present studies found that the IgG2a version of clone 54 4-1BB antibody amplified and matured tumor infiltrating CD8 T cells very efficiently.

Accordingly, in certain embodiments, the present disclo-sure provides human 4-1BB agonist antibodies, particularly a 4-1BB IgG2a agonist monoclonal antibody. The present antibodies may be manufactured under GMP-compliant conditions. The present antibodies may be used in patients in a monospecific or bi-specific format. In further aspects, the present antibodies may be administered as immunotherapy alone or in conjunction with additional immunotherapy, such as immune checkpoint inhibitors (e.g., anti-PD1 or anti-CTLA4 antibodies), to patients with cancer.

I. Definitions

As used herein, "essentially free," in terms of a specified component, is used herein to mean that none of the specified component has been purposefully formulated into a com-position and/or is present only as a contaminant or in trace amounts. The total amount of the specified component resulting from any unintended contamination of a compo-sition is therefore well below 0.05%, preferably below 0.01%. Most preferred is a composition in which no amount of the specified component can be detected with standard analytical methods.

As used herein the specification, "a" or "an" may mean one or more. As used herein in the claim(s), when used in conjunction with the word "comprising," the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alterna-tives and "and/or." As used herein "another" may mean at least a second or more. The term "about" means in general, the stated value plus or minus 5%.

"Treatment" and "treating" refer to administration or application of a therapeutic agent to a subject or perfor-mance of a procedure or modality on a subject for the purpose of obtaining a therapeutic benefit of a disease or health-related condition.

"Subject" and "patient" refer to either a human or non-human, such as primates, mammals, and vertebrates. In particular embodiments, the subject is a human.

The term "therapeutic benefit" or "therapeutically effec-tive" as used throughout this application refers to anything that promotes or enhances the well-being of the subject with respect to the medical treatment of this condition. This includes, but is not limited to, a reduction in the frequency or severity of the signs or symptoms of a disease. For example, treatment of cancer may involve, for example, a reduction in the size of a tumor, a reduction in the invasive-ness of a tumor, reduction in the growth rate of the cancer, or prevention of metastasis. Treatment of cancer may also refer to prolonging survival of a subject with cancer.

An "anti-cancer" agent is capable of negatively affecting a cancer cell/tumor in a subject, for example, by promoting killing of cancer cells, inducing apoptosis in cancer cells, reducing the growth rate of cancer cells, reducing the incidence or number of metastases, reducing tumor size, inhibiting tumor growth, reducing the blood supply to a tumor or cancer cells, promoting an immune response against cancer cells or a tumor, preventing or inhibiting the progression of cancer, or increasing the lifespan of a subject with cancer.

The term "antibody" herein is used in the broadest sense and specifically covers monoclonal antibodies (including full length monoclonal antibodies), polyclonal antibodies, multispecific antibodies (e.g., bispecific antibodies), and antibody fragments so long as they exhibit the desired biological activity.

The term "monoclonal antibody" as used herein refers to an antibody obtained from a population of substantially homogeneous antibodies, e.g., the individual antibodies comprising the population are identical except for possible mutations, e.g., naturally occurring mutations, that may be present in minor amounts. Thus, the modifier "monoclonal" indicates the character of the antibody as not being a mixture of discrete antibodies. In certain embodiments, such a mono-clonal antibody typically includes an antibody comprising a polypeptide sequence that binds a target, wherein the target-binding polypeptide sequence was obtained by a process that includes the selection of a single target binding polypeptide sequence from a plurality of polypeptide sequences. For example, the selection process can be the selection of a unique clone from a plurality of clones, such as a pool of hybridoma clones, phage clones, or recombinant DNA clones. It should be understood that a selected target binding sequence can be further altered, for example, to improve affinity for the target, to humanize the target binding sequence, to improve its production in cell culture, to reduce its immunogenicity in vivo, to create a multispecific anti-body, etc., and that an antibody comprising the altered target binding sequence is also a monoclonal antibody of this invention. In contrast to polyclonal antibody preparations, which typically include different antibodies directed against different determinants (epitopes), each monoclonal antibody of a monoclonal antibody preparation is directed against a single determinant on an antigen. In addition to their speci-ficity, monoclonal antibody preparations are advantageous in that they are typically uncontaminated by other immu-noglobulins.

The terms "contacted" and "exposed," when applied to a cell, are used herein to describe the process by which a therapeutic construct and a chemotherapeutic or radiothera-peutic agent are delivered to a target cell or are placed in direct juxtaposition with the target cell. To achieve cell killing, for example, both agents are delivered to a cell in a combined amount effective to kill the cell or prevent it from dividing.

The term "immune checkpoint" refers to a molecule such as a protein in the immune system which provides inhibitory signals to its components in order to balance immune reactions. Known immune checkpoint proteins comprise CTLA-4, PD1 and its ligands PD-L1 and PD-L2 and in addition LAG-3, BTLA, B7H3, B7H4, TIM3, KIR. The pathways involving LAG3, BTLA, B7H3, B7H4, TIM3, and KIR are recognized in the art to constitute immune check-point pathways similar to the CTLA-4 and PD-1 dependent pathways (see e.g. Pardoll, 2012; Mellman et al., 2011).

An "immune checkpoint inhibitor" refers to any com-pound inhibiting the function of an immune checkpoint protein. Inhibition includes reduction of function and full blockade. In particular the immune checkpoint protein is a human immune checkpoint protein. Thus, the immune checkpoint protein inhibitor in particular is an inhibitor of a human immune checkpoint protein.

II. Anti-41BB Antibodies

In certain embodiments, an antibody or a fragment thereof that binds to at least a portion of 4-1BB and activates signaling, such as to stimulate an immune response, is contemplated. As used herein, the term "antibody" is intended to refer broadly to any immunologic binding agent, such as IgG, IgM, IgA, IgD. IgE, and genetically modified IgG as well as polypeptides comprising antibody CDR domains that retain antigen binding activity. The antibody may be selected from the group consisting of a chimeric antibody, an affinity matured antibody, a polyclonal antibody, a monoclonal antibody, a humanized antibody, a human antibody, or an antigen-binding antibody fragment or a natural or synthetic ligand. Preferably, the anti-41BB antibody is a monoclonal antibody or a humanized antibody.

In some embodiments, the anti-41BB antibody comprises CDRs 1-3 of the heavy chain of SEQ ID NO:2 (GYSFT- DYN (SEQ ID NO:3), INPNYGTT (SEQ ID NO:5), and ARSPVEDYFDY (SEQ ID NO:7)) and the CDRs 1-3 of the light chain of SEQ ID NO:10 (SSVSSSY (SEQ ID NO:11), STS (SEQ ID NO:13), and QQYSGYPLIT (SEQ ID NO:15)). The anti-41BB antibody may have at least 80%, such as 85%, 90%, 91%, 92%, 93%, 94%, 95%, 96%, 97%, 98%, 99%, or 100%, sequence identity to SEQ ID NOs: 1, 2, 9, or 10. The anti-41BB antibody may have at least 80%, such as 85%, 90%, 91%, 92%, 93%, 94%, 95%, 96%, 97%, 98%, 99%, or 100%, sequence identity to SEQ ID NOs: 17, 18, 25, or 26. The anti-41BB antibody may have at least 80%, such as 85%, 90%, 91%, 92%, 93%, 94%, 95%, 96%, 97%, 98%, 99%, or 100%, sequence identity to SEQ ID NOs: 33, 34, 41, or 42. The anti-41BB antibody may have at least 80%, such as 85%, 90%, 91%, 92%, 93%, 94%, 95%, 96%, 97%, 98%, 99%, or 100%, sequence identity to SEQ ID NOs: 49, 50, 57, or 58. The heavy and light chain sequences are depicted below.

```
Clone 54 4-1BB VH Consensus Sequence starting from
Frame 1 (FR1) (position 77-505) IgG2a
Nucleotide sequence:
                                                (SEQ ID NO: 1)
GAGTTCCAGCTGCAGCAGTCTGGACCTGAGCTGGTGAAGCCTGGCGCTTCAGTG

AAGATATCCTGCAAGGCTTCTGGTTACTCATTCACTGACTACAACATGAACTGGG

TGAAGCAGAGCAATGGAAAGAGCCTTGAGTGGATTGGAGTAATTAATCCTAACT

ATGGTACTACTAGCTACAATCAGAAGTTCAAGGGCAAGGCCACATTTACTGTAG

ACCAATCTTCCAGCACAGCCTACATGCAGCTCAACAGCCTGACATCTGAGGACTC

TGCAGTCTATTACTGTGCAAGATCCCCGGTAGAGGACTACTTTGACTACTGGGGC

CAAGGCACCACTCTCACAGTCTCCTCAGCCAAAACAACAGCCCCATCGGTCTATC

CACTGGCCCCTGTGTGTGGAGGTACAACTGGCTCCTCGGTGACTCTA

Amino acid sequence:
                                                (SEQ ID NO: 2)
EFQLQQSGPELVKPGASVKISCKASGYSFTDYNMNWVKQSNGKSLEWIGVINPNYG

TTSYNQKFKGKATFTVDQSSSTAYMQLNSLTSEDSAVYYCARSPVEDYFDYWGQGT

TLTVSSAKTTAPSVYPLAPVCGGTTGSSVTL

CDR1:
                                                (SEQ ID NO: 3)
GYSFTDYN (SEQ ID NO: 4)
GTTACTCATTCACTGACTACAAC

CDR2:
                                                (SEQ ID NO: 5)
INPNYGTT (SEQ ID NO: 6)
ATTAATCCTAACTATGGTACTACT

CDR3:
                                                (SEQ ID NO: 7)
ARSPVEDYFDY (SEQ ID NO: 8)
GCAAGATCCCCGGTAGAGGACTACTTTGACTAC

VL Consensus Sequence starting from Frame 1 (FR1)
(position 91-470)
Nucleotide sequence:
                                                (SEQ ID NO: 9)
GAAAATGTGCTCACCCAGTCTCCAGCAATCATGTCTGCATCTCCAGGGGAAAAG

GTCACCATGACCTGCAGGGCCAGGTCAAGTGAAGTTCCAGTTACTTGCACTGGT

ACCAGCAGAAGTCAGGTGCCTCCCCCAAACTCTGGATTTATAGCACATCCAACTT
```

GGCTTCTGGAGTCCCTGCTCGCTTCAGTGGCAGTGGGTCTGGGACCTCTTACTCT

CTCACAATCAGCAGTGTGGAGGCTGAAGATCCTGCCACTTATTACTGCCAGCAGT

ACAGTGGTTACCCACTCATCACGTTCGGTGCTGGGACCAAGCTGGA

GCTGAAACGGGCTGATGCTGCACCAACTGTATCCATCTTCCCACCATCCAGTGAG

CAGTT

Amino acid sequence:
                                              (SEQ ID NO: 10)
ENVLTQSPAIMSASPGEKVTMTCRARSSVSSSYLHWYQQKSGASPKLWIYSTSNLAS

GVPARFSGSGSGTSYSLTISSVEAEDAATYYCQQYSGYPLITFGAGTKLELKRADAAP

TVSIFPPSSEQ

CDR1:
                                              (SEQ ID NO: 11)
SSVSSSY (SEQ ID NO: 12)
TCAAGTGTAAGTTCCAGTTAC

CDR2:
                                              (SEQ ID NO: 13)
STS (SEQ ID NO: 14)
AGCACATCC

CDR3:
                                              (SEQ ID NO: 15)
QQYSGYPLIT (SEQ ID NO: 16)
CAGCAGTACAGTGGTTACCCACTCATCACG

Clone 135B 4-1BB VH Consensus Sequence starting from
Frame 1 (FR1) (position 45-407) IgG1
Nucleotide sequence:
                                              (SEQ ID NO: 17)
AGGTGAAGCTGCAGCAGTCAGGACCTGAGCTGGTGAAGCCTGGGGCTTCAGTGA

AGATATCCTGTAAGGCTTCTGGATACACGTTCACTGACTACTACATGAACTGGGT

GAAGCAGAGCCATGGAAAGAGCCTTGAGTGGATTGGAGATATTAATCCTAACAA

TGATGGTACTACCTACTACAACCAGAAGTTCAAGGGCAAGGCCACATTGACTGT

AGACAAGTCCTCCAGCACAGCCTACATGGAGCTCCGCAGCCTGACATCTGAGGA

CTCTGCAGTCTATTACTGTGCAAGATCCCTCTACGGTAGTAGCTACTACTTTGACT

ACTGGGGCCAAGGCACCACTCTCACAGTCTCCTCAG

Amino acid sequence:
                                              (SEQ ID NO: 18)
VKLQQSGPELVKPGASVKTSCKASGYTFTDYYMNWVKQSHGKSLEWIGDINPNNDG

TTYYNQKFKGKATLTVDKSSSTAYMELRSLTSEDSAVYYCARSLYGSSYYFDYWGQ
GTTLTVSS

CDR1:
                                              (SEQ ID NO: 19)
GYTFTDYY (SEQ ID NO: 20)
GGATACACGTTCACTGACTACTAC

CDR2:
                                              (SEQ ID NO: 21)
INPNNDGT
                                              (SEQ ID NO: 22)
ATTAATCCTAACAATGATGGTACT

-continued

CDR3:

(SEQ ID NO: 23)

ARSLYGSSYYFDY (SEQ ID NO: 24)

GCAAGATCCCTCTACGGTAGTAGCTACTACTTTOACTAC

VL Consensus Sequence starting from Frame 1 (FR1)
(position 46-379)
Nucleotide sequence:

(SEQ ID NO: 25)

GATATTGTGATGACACAGTCTCCTGCTTCCTTAGCTGTATCTCTGGGGCAGAGGG

CCACCATCTCATACAGGGCCAGCAAAAGTGTCAGTACATCTGGCTATAGTTATAT

GCACTGGAACCAACAGAAACCAGGACAGCCACCCAGACTCCTCATCTATCTTGT

ATCCAACCTAGAATCTGGGATCCCAGCCAGGTTTAGTGGCAGTGGGTCTGGGAC

AGACTTCACCCTCAACATCCATCCTGTGGAGGAGGAGGATGCTGCAACCTATTAC

TGTCAGCAAAGTAATGAGGACCCGTGGACGTTCGGTGGAGGCACCAAGCTGGAA

ATCAAAC

Amino acid sequence:

(SEQ ID NO: 26)

DIVMTQSPASLAVSLGQRATISYRASKSVSTSGYSYMHWNQQKPGQPPRLLIYLVSN

LESGIPARFSGSGSGTDFTLNIHPVEEEDAATYYCQQSNEDPWTFGGGTKLEIK

CDR1:

(SEQ ID NO: 27)

KSVSTSGYSY (SEQ ID NO: 28)

AAAAGTGTCAGTACATCTGGCTATAGTTAT

CDR2:

(SEQ ID NO: 29)

LVS (SEQ ID NO: 30)

CTTGTATCC

CDR3:

(SEQ ID NO: 31)

QQSNEDPWT (SEQ ID NO: 32)

CAGCAAAGTAATGAGGACCCGTGGACG

Clone 138 4-1BB VH Consensus Sequence starting from
Frame 1 (FR1) (position 56-409) IgG2b
Nucleotide sequence:

(SEQ ID NO: 33)

AGGTGCAGCTGCAGGAGTCTGGGGGAGGCTTAGTGAAGCCTGGAGGGTCCCTGA

AACTCTCCTGTGCAGCCTCTGGATTCACTTTCAGTGACTATGGAATGCACTGGGT

TCGTCAGGCTCCAGAGAAGGGGCTGGAGTGGGTTGCATACATTAGTAGTGGCAG

TAATTCCATCTACTATGCAGACACAGTGACGGGCCGATTCACCATCTCCAGAGAC

AATGCCAAGAACACCCTGTTCCTGCAAATGACCAGTCTGAGGTCTGAGGACACG

GCCATGTATTACTGTGCCTCGAATAATGGTTACTTCTACTTTGACTACTGGGGCC

AAGGCACCACTCTCACAGTCTCCTCAG

Amino acid sequence:

(SEQ ID NO: 34)

VQLQESGGGLVKPGGSLKLSCAASGFTFSDYGMHWVRQAPEKGLEWVAYISSGSNS

IYYADTVTGRFTISRDNAKNTLFLQMTSLRSEDTAMYYCASNNGYFYFDYWGQGTT

LTVSS

-continued

CDR1:

(SEQ ID NO: 35)

GFTFSDYG (SEQ ID NO: 36)

GGATTCACTTTCAGTGACTATGGA

CDR2:

(SEQ ID NO: 37)

ISSGSNSI (SEQ ID NO: 38)

ATTAGTAGTGGCAGTAATTCCATC

CDR3:

(SEQ ID NO: 39)

ASNNGYFYFDY (SEQ ID NO: 40)

GCCTCGAATAATGGTTACTTCTACTTTGACTAC

VL Consensus Sequence starting from Frame 1 (FR1)
(position 63-378)
Nucleotide sequence:

(SEQ ID NO: 41)

ATTGTGATCACCCAGTCTCCAGCAATCCTGTCTGCATCTCCAGGGGAGAAGGTCA

CAATGACTTGCAGGGCCAGCTCAAGTGTAAGTTACATGCACTGGTACCAGCAGA

AGCCAGGATCCTCCCCCAAACCCTGGATTTATGCCACATCCAACCTGGCTTCTGG

AGTCCCTGCTCGCTTCAGTGGCAGTGGGTCTGGGACCTCTTACTCTCTCACAGTC

AGCAGAGTGGAGGCTGAAGATGCTGCCACTTATTACTGCCAGCAGTGGAGTAGT

GACCCATTCACGTTCGGCTCGGGGACAAAGTTGGAAATAAAAC

Amino acid sequence:

(SEQ ID NO: 2)

IVTTQSPAILSASPGEKVTMTCRASSSVSYMHWYQQKPGSSPKPWIYATSNLASGVPA

RFSGSGSGTSYSLTVSRVEAEDAATYYCQQWSSDPFTFGSGTKLEIK

CDR1:

(SEQ ID NO: 43)

SSVSY (SEQ ID NO: 44)

TCAAGTGTAAGTTAC

CDR2:

(SEQ ID NO: 45)

ATS (SEQ ID NO: 46)

GCCACATCC

CDR3:

(SEQ ID NO: 47)

QQWSSDPFT (SEQ ID NO: 48)

CAGCAGTGGAGTAGTGACCCATTCACG

Clone 49A 4-1BB VH Consensus Sequence starting from
Frame 1 (FR1) (position 65-427) IgG1
Nucleotide sequence:

(SEQ ID NO: 49)

AGGTGAAACTGCAGCAGTCAGGACCTGAGCTGGTGAAGCCTGGGGCTTCAGTGA

AGATATCCTGTAAGGCTTCTGGATACACGITCACTGACTACTACATGAACTGGGT

GAAGGAGAGCCATGGAAAGAGCCTTGAGrGGAITGGAGATArTAATCCTAACAA

TGGTGGTTCTACCTACTACAACCAGAAGTTCAAGGGCAAGGCCACATTGACTGTA

GAGAAGTCCTCCAGCACAGCCTTCATGGAGCTCCGCAGCCTGACATCTGAGGAC

TCTGCAGTCTATTACTGTGCAAGATCCCTCTACGGTAGTACCTACTACTTTGACTA

-continued

CTGGGGCCAAGGCACCCCTCTCACAGTCTCCTCAG

Amino acid sequence:

(SEQ ID NO: 50)

VKLQQSGPELVKPGASVK1SCKASGYTFTDYYMNWVKESHGKSLEWIGDINPNNGG

STYYNQKFKGKATLTVEKSSSTAFMELRSLTSEDSAVYYCARSLYQSTYYFDYWGQ

GTPLTVSS

CDR1:

(SEQ ID NO: 1)

GYIFIDYY (SEQ ID NO: 52)

GGATACACGTTCACTGACTACTAC

CDR2:

(SEQ ID NO: 53)

INPNNGGS (SEQ ID NO: 54)

ATTAATCCTAACAATGGTGGTTCT

CDR3:

(SEQ ID NO: 55)

ARSLYGSTYYFDY (SEQ ID NO: 56)

GCAAGATCCCTCTACGGTAGTACCTACTACTTTGACTAC

VL Consensus Sequence starting from Frame 1 (FR1)
(position 55-388)
Nucleotide sequence:

(SEQ ID NO: 57)

GATATTGTGCTGACCCAGTCTCCAGCTTCTTTGGCTGTGTCTCTAGGGCAGAGGG

CCACCATCTCCTGCAAGGCCAGCCAAAGTGTTGATTATGATGGTGATAGTTATAT

GAACTGGTACCAACAGAAGCCAGGACAGCCACCCAAACTCCTCATCTATGCTGC

ATCCAATCTAGAATCTGGGATCCCAGCCAGGTTTAGTGGCAGTGGGTCTGGGAC

AGACTTCACTCTCAACATCCATCCTGTGGAGGAGGAGGATGCTGGAACCTATTAC

TGTCAGCAAAGTAATGACGATCCGTGGACGTTCGGTGGAGGCACCAAGCTGGAA

ATCAAAC

Amino acid sequence:

(SEQ ID NO: 58)

DIVLTQSPASLAVSLGQRATISCKASQSVDYDGDSYMNWYQQKPGQPPKLLIYAASN

LESGIPARFSGSGSGTDFTLNIHPVEEEDAGTYYCQQSNDDPWTFGGGTKLEIK

CDR1:

(SEQ ID NO: 59)

QSVDYDGDSY (SEQ ID NO: 60)

CAAAGTGTTGATTATGATGGTGATAGTTAT

CDR2:

(SEQ ID NO: 61)

AAS (SEQ ID NO: 62)

GCTGCATCC

CDR3:

(SEQ ID NO: 63)

QQSNDDPWT (SEQ ID NO: 64)

CAGCAAAGTAATGACGATCCGTGGACG

Thus, by known means and as described herein, poly-clonal or monoclonal antibodies, antibody fragments, and binding domains and CDRs (including engineered forms of any of the foregoing) may be created that are specific to 4-1BB, one or more of its respective epitopes, or conjugates of any of the foregoing, whether such antigens or epitopes are isolated from natural sources or are synthetic derivatives or variants of the natural compounds.

Examples of antibody fragments suitable for the present embodiments include, without limitation: (i) the Fah frag-ment, consisting of $V_L$, $V_H$, $C_L$, and $C_{H1}$ domains; (ii) the "Fd" fragment consisting of the $V_H$ and $C_{H1}$ domains; (iii) the "Fv" fragment consisting of the $V_L$ and $V_H$ domains of a single antibody; (iv) the "dAb" fragment, which consists of a $V_H$ domain; (v) isolated CDR regions; (vi) F(ab')2 fragments, a bivalent fragment comprising two linked Fab fragments; (vii) single chain Fv molecules ("scFv"), wherein a $V_H$ domain and a $V_L$ domain are linked by a peptide linker that allows the two domains to associate to form a binding domain; (viii) bi-specific single chain Fv dimers (see U.S. Pat. No. 5,091,513); and (ix) diabodies, multivalent or multispecific fragments constructed by gene fusion (US Patent App. Pub. 20050214860). Fv, scFv, or diabody mol-ecules may be stabilized by the incorporation of disulphide bridges linking the $V_H$ and $V_L$ domains. Minibodies com-prising a scFv joined to a CH3 domain may also be made (Hu et al., 1996).

Antibody-like binding peptidomimetics are also contem-plated in embodiments. Liu et al. (2003) describe "antibody like binding peptidomimetics" (ABiPs), which are peptides that act as pared-down antibodies and have certain advan-tages of longer serum half-life as well as less cumbersome synthesis methods.

Animals may be inoculated with an antigen, such as a 4-1BB extracellular domain (ECD) protein, in order to produce antibodies specific for 4-1BB. Frequently an anti-gen is bound or conjugated to another molecule to enhance the immune response. As used herein, a conjugate is any peptide, polypeptide, protein, or non-proteinaceous sub-stance bound to an antigen that is used to elicit an immune response in an animal. Antibodies produced in an animal in response to antigen inoculation comprise a variety of non-identical molecules (polyclonal antibodies) made from a variety of individual antibody producing B lymphocytes. A polyclonal antibody is a mixed population of antibody species, each of which may recognize a different epitope on the same antigen. Given the correct conditions for poly-clonal antibody production in an animal, most of the anti-bodies in the animal's serum will recognize the collective epitopes on the antigenic compound to which the animal has been immunized. This specificity is further enhanced by affinity purification to select only those antibodies that recognize the antigen or epitope of interest.

A monoclonal antibody is a single species of antibody wherein every antibody molecule recognizes the same epitope because all antibody producing cells are derived from a single B-lymphocyte cell line. The methods for generating monoclonal antibodies (MAbs) generally begin along the same lines as those for preparing polyclonal antibodies. In some embodiments, rodents such as mice and rats are used in generating monoclonal antibodies. In some embodiments, rabbit, sheep, or frog cells are used in gen-erating monoclonal antibodies. The use of rats is well known and may provide certain advantages. Mice (e.g., BALB/c mice) are routinely used and generally give a high percent-age of stable fusions.

Hybridoma technology involves the fusion of a single B lymphocyte from a mouse previously immunized with a 4-1BB antigen with an immortal myeloma cell (usually mouse myeloma). This technology provides a method to propagate a single antibody-producing cell for an indefinite number of generations, such that unlimited quantities of structurally identical antibodies having the same antigen or epitope specificity (monoclonal antibodies) may be pro-duced.

Plasma B cells (CD45$^+$CD5$^-$CD19$^+$) may be isolated from freshly prepared rabbit peripheral blood mononuclear cells of immunized rabbits and further selected for 4-1BB binding cells. After enrichment of antibody producing B cells, total RNA may be isolated and cDNA synthesized. DNA sequences of antibody variable regions from both heavy chains and light chains may be amplified, constructed into a phage display Fab expression vector, and transformed into E. coli. 4-1BB specific binding Fab may be selected out through multiple rounds enrichment panning and sequenced. Selected 4-1BB binding hits may be expressed as full-length IgG in rabbit and rabbit/human chimeric forms using a mammalian expression vector system in human embryonic kidney (HEK293) cells (Invitrogen) and purified using a protein G resin with a fast protein liquid chromatography (FPLC) separation unit.

In one embodiment, the antibody is a chimeric antibody, for example, an antibody comprising antigen binding sequences from a non-human donor grafted to a heterolo-gous non-human, human, or humanized sequence (e.g., framework and/or constant domain sequences). Methods have been developed to replace light and heavy chain constant domains of the monoclonal antibody with analo-gous domains of human origin, leaving the variable regions of the foreign antibody intact. Alternatively, "fully human" monoclonal antibodies are produced in mice transgenic for human immunoglobulin genes. Methods have also been developed to convert variable domains of monoclonal anti-bodies to more human form by recombinantly constructing antibody variable domains having both rodent, for example, mouse, and human amino acid sequences. In "humanized" monoclonal antibodies, only the hypervariable CDR is derived from mouse monoclonal antibodies, and the frame-work and constant regions are derived from human amino acid sequences (see U.S. Pat. Nos. 5,091,513 and 6,881, 557). It is thought that replacing amino acid sequences in the antibody that are characteristic of rodents with amino acid sequences found in the corresponding position of human antibodies will reduce the likelihood of adverse immune reaction during therapeutic use. A hybridoma or other cell producing an antibody may also be subject to genetic mutation or other changes, which may or may not alter the binding specificity of antibodies produced by the hybridoma.

Methods for producing polyclonal antibodies in various animal species, as well as for producing monoclonal anti-bodies of various types, including humanized, chimeric, and fully human, are well known in the art and highly predict-able. For example, the following U.S. patents and patent applications provide enabling descriptions of such methods: U.S. Patent Application Nos. 2004/0126828 and 2002/0172677; and U.S. Pat. Nos. 3,817,837; 3,850,752; 3,939,350; 3,996,345; 4,196,265; 4,275,149; 4,277,437; 4,366,241; 4,469,797; 4,472,509; 4,606,855; 4,703,003; 4,742,159; 4,767,720; 4,816,567; 4,867,973; 4,938,948; 4,946,778; 5,021,236; 5,164,296; 5,196,066; 5,223,409; 5,403,484; 5,420,253; 5,565,332; 5,571,698; 5,627,052; 5,656,434; 5,770,376; 5,789,208; 5,821,337; 5,844,091; 5,858, 657; 5,861,155; 5,871,907; 5,969,108; 6,054,297; 6,165, 464; 6,365,157; 6,406,867; 6,709,659; 6,709,873; 6,753, 407; 6,814,965; 6,849,259; 6,861,572; 6,875,434; and 6,891,024. All patents, patent application publications, and other publications cited herein and therein are hereby incorporated by reference in the present application.

Antibodies may be produced from any animal source, including birds and mammals. Preferably, the antibodies are ovine, murine (e.g., mouse and rat), rabbit, goat, guinea pig, camel, horse, or chicken. In addition, newer technology permits the development of and screening for human antibodies from human combinatorial antibody libraries. For example, bacteriophage antibody expression technology allows specific antibodies to be produced in the absence of animal immunization, as described in U.S. Pat. No. 6,946, 546, which is incorporated herein by reference. These techniques are further described in: Marks (1992); Stemmer (1994); Gram et al. (1992); Barbas et al. (1994); and Schier et al. (1996).

It is fully expected that antibodies to 4-1BB will have the ability to neutralize or counteract the effects of 4-1BB regardless of the animal species, monoclonal cell line, or other source of the antibody. Certain animal species may be less preferable for generating therapeutic antibodies because they may be more likely to cause allergic response due to activation of the complement system through the "Fc" portion of the antibody. However, whole antibodies may be enzymatically digested into "Fc" (complement binding) fragment, and into antibody fragments having the binding domain or CDR. Removal of the Fc portion reduces the likelihood that the antigen antibody fragment will elicit an undesirable immunological response, and thus, antibodies without Fc may be preferential for prophylactic or therapeutic treatments. As described above, antibodies may also be constructed so as to be chimeric or partially or fully human, so as to reduce or eliminate the adverse immunological consequences resulting from administering to an animal an antibody that has been produced in, or has sequences from, other species.

Substitutional variants typically contain the exchange of one amino acid for another at one or more sites within the protein, and may be designed to modulate one or more properties of the polypeptide, with or without the loss of other functions or properties. Substitutions may be conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine. Alternatively, substitutions may be non-conservative such that a function or activity of the polypeptide is affected. Non-conservative changes typically involve substituting a residue with one that is chemically dissimilar, such as a polar or charged amino acid for a nonpolar or uncharged amino acid, and vice versa.

Proteins may be recombinant, or synthesized in vitro. Alternatively, a non-recombinant or recombinant protein may be isolated from bacteria. It is also contemplated that a bacteria containing such a variant may be implemented in compositions and methods. Consequently, a protein need not be isolated.

It is contemplated that in compositions there is between about 0.001 mg and about 10 mg of total polypeptide, peptide, and/or protein per ml. Thus, the concentration of protein in a composition can be about, at least about or at most about 0.001, 0.010, 0.050, 0.1, 0.2, 0.3, 0.4, 0.5, 0.6, 0.7, 0.8, 0.9, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0 mg/ml or more (or any range derivable therein). Of this, about, at least about, or at most about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% may be an antibody that binds 4-1BB.

An antibody or preferably an immunological portion of an antibody, can be chemically conjugated to, or expressed as, a fusion protein with other proteins. For purposes of this specification and the accompanying claims, all such fused proteins are included in the definition of antibodies or an immunological portion of an antibody.

Embodiments provide antibodies and antibody-like molecules against 4-1BB, polypeptides and peptides that are linked to at least one agent to form an antibody conjugate or payload. In order to increase the efficacy of antibody molecules as diagnostic or therapeutic agents, it is conventional to link or covalently bind or complex at least one desired molecule or moiety. Such a molecule or moiety may be, but is not limited to, at least one effector or reporter molecule. Effector molecules comprise molecules having a desired activity, e.g., cytotoxic activity. Non-limiting examples of effector molecules that have been attached to antibodies include toxins, therapeutic enzymes, antibiotics, radio-labeled nucleotides and the like. By contrast, a reporter molecule is defined as any moiety that may be detected using an assay. Non-limiting examples of reporter molecules that have been conjugated to antibodies include enzymes, radiolabels, haptens, fluorescent labels, phosphorescent molecules, chemiluminescent molecules, chromophores, luminescent molecules, photoaffinity molecules, colored particles or ligands, such as biotin.

Several methods are known in the art for the attachment or conjugation of an antibody to its conjugate moiety. Some attachment methods involve the use of a metal chelate complex employing, for example, an organic chelating agent such a diethylenetriaminepentaacetic acid anhydride (DTPA); ethylenetriaminetetraacetic acid; N-chloro-p-toluenesulfonamide; and/or tetrachloro-3-6?-diphenylglycouril-3 attached to the antibody. Monoclonal antibodies may also be reacted with an enzyme in the presence of a coupling agent such as glutaraldehyde or periodate. Conjugates with fluorescein markers are prepared in the presence of these coupling agents or by reaction with an isothiocyanate.

II. Treatment of Diseases

Certain aspects of the present embodiments can be used to prevent or treat a disease or disorder associated with 4-1BB signaling. The present 4-1BB antibodies may be used in the treatment of a disease, such as a cancer, infectious disease, inflammatory disease, or autoimmune disease. Further methods are provided for administering a vaccine. Suitable vaccines include, for example, a tumor cell vaccine, a DNA vaccine, a GM-CSF-modified tumor cell vaccine, or an antigen-loaded dendritic cell vaccine.

In certain embodiments, the compositions and methods of the present embodiments involve an antibody or an antibody fragment against 4-1BB to activate its activity in cancer cell proliferation, in combination with a second or additional therapy.

Accordingly, in some embodiments, provided herein are methods for treating or delaying progression of cancer in an individual comprising administering to the individual an effective amount an anti-41BB antibody. Examples of cancers contemplated for treatment include lung cancer, head and neck cancer, breast cancer, pancreatic cancer, prostate cancer, renal cancer, bone cancer, testicular cancer, cervical cancer, gastrointestinal cancer, lymphomas, pre-neoplastic lesions in the lung, colon cancer, melanoma, and bladder cancer.

In some embodiments, the individual has cancer that is resistant (has been demonstrated to be resistant) to one or more anti-cancer therapies. In some embodiments, resistance to anti-cancer therapy includes recurrence of cancer or refractory cancer. Recurrence may refer to the reappearance of cancer, in the original site or a new site, after treatment. In some embodiments, resistance to anti-cancer therapy includes progression of the cancer during treatment with the anti-cancer therapy. In some embodiments, the cancer is at early stage or at late stage.

A. Pharmaceutical Preparations

Where clinical application of a therapeutic composition containing an inhibitory antibody is undertaken, it will generally be beneficial to prepare a pharmaceutical or therapeutic composition appropriate for the intended application. In certain embodiments, pharmaceutical compositions may comprise, for example, at least about 0.1% of an active compound. In other embodiments, an active compound may comprise between about 2% to about 75% of the weight of the unit, or between about 25% to about 60%, for example, and any range derivable therein.

The therapeutic compositions of the present embodiments are advantageously administered in the form of injectable compositions either as liquid solutions or suspensions; solid forms suitable for solution in, or suspension in, liquid prior to injection may also be prepared. These preparations also may be emulsified.

The phrases "pharmaceutical or pharmacologically acceptable" refers to molecular entities and compositions that do not produce an adverse, allergic, or other untoward reaction when administered to an animal, such as a human, as appropriate. The preparation of a pharmaceutical composition comprising an antibody or additional active ingredient will be known to those of skill in the art in light of the present disclosure. Moreover, for animal (e.g., human) administration, it will be understood that preparations should meet sterility, pyrogenicity, general safety, and purity standards as required by FDA Office of Biological Standards.

As used herein, "pharmaceutically acceptable carrier" includes any and all aqueous solvents (e.g., water, alcoholic/aqueous solutions, saline solutions, parenteral vehicles, such as sodium chloride, Ringer's dextrose, etc.), non-aqueous solvents (e.g., propylene glycol, polyethylene glycol, vegetable oil, and injectable organic esters, such as ethyloleate), dispersion media, coatings, surfactants, antioxidants, preservatives (e.g., antibacterial or antifungal agents, anti-oxidants, chelating agents, and inert gases), isotonic agents, absorption delaying agents, salts, drugs, drug stabilizers, gels, binders, excipients, disintegration agents, lubricants, sweetening agents, flavoring agents, dyes, fluid and nutrient replenishers, such like materials and combinations thereof, as would be known to one of ordinary skill in the art. The pH and exact concentration of the various components in a pharmaceutical composition are adjusted according to well-known parameters.

The term "unit dose" or "dosage" refers to physically discrete units suitable for use in a subject, each unit containing a predetermined quantity of the therapeutic composition calculated to produce the desired responses discussed above in association with its administration, i.e., the appropriate route and treatment regimen. The quantity to be administered, both according to number of treatments and unit dose, depends on the effect desired. The actual dosage amount of a composition of the present embodiments administered to a patient or subject can be determined by physical and physiological factors, such as body weight, the age, health, and sex of the subject, the type of disease being treated, the extent of disease penetration, previous or concurrent therapeutic interventions, idiopathy of the patient, the route of administration, and the potency, stability, and toxicity of the particular therapeutic substance. For example, a dose may also comprise from about 1 µg/kg/body weight to about 1000 mg/kg/body weight (this such range includes intervening doses) or more per administration, and any range derivable therein. In non-limiting examples of a derivable range from the numbers listed herein, a range of about 5 µg/kg/body weight to about 100 mg/kg/body weight, about 5 µg/kg/body weight to about 500 mg/kg/body weight, etc., can be administered. The practitioner responsible for administration will, in any event, determine the concentration of active ingredient(s) in a composition and appropriate dose(s) for the individual subject.

The active compounds can be formulated for parenteral administration, e.g., formulated for injection via the intravenous, intramuscular, sub-cutaneous, or even intraperitoneal routes. Typically, such compositions can be prepared as either liquid solutions or suspensions; solid forms suitable for use to prepare solutions or suspensions upon the addition of a liquid prior to injection can also be prepared; and, the preparations can also be emulsified.

The pharmaceutical forms suitable for injectable use include sterile aqueous solutions or dispersions; formulations including sesame oil, peanut oil, or aqueous propylene glycol; and sterile powders for the extemporaneous preparation of sterile injectable solutions or dispersions. In all cases the form must be sterile and must be fluid to the extent that it may be easily injected. It also should be stable under the conditions of manufacture and storage and must be preserved against the contaminating action of microorganisms, such as bacteria and fungi.

The proteinaceous compositions may be formulated into a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

A pharmaceutical composition can include a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion, and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

B. Combination Treatments

In certain embodiments, the compositions and methods of the present embodiments involve an antibody or an antibody fragment against 4-1BB to activate its activity, in combination with a second or additional therapy. For example, the disease may be cancer.

The methods and compositions, including combination therapies, enhance the therapeutic or protective effect, and/or increase the therapeutic effect of another anti-cancer or anti-hyperproliferative therapy. Therapeutic and prophylactic methods and compositions can be provided in a combined amount effective to achieve the desired effect, such as the killing of a cancer cell and/or the inhibition of cellular hyperproliferation. This process may involve contacting the cells with both an antibody or antibody fragment and a second therapy. A tissue, tumor, or cell can be contacted with one or more compositions or pharmacological formulation(s) comprising one or more of the agents (i.e., antibody or antibody fragment or an anti-cancer agent), or by contacting the tissue, tumor, and/or cell with two or more distinct compositions or formulations, wherein one composition provides 1) an antibody or antibody fragment, 2) an anti-cancer agent, or 3) both an antibody or antibody fragment and an anti-cancer agent. Also, it is contemplated that such a combination therapy can be used in conjunction with chemotherapy, radiotherapy, surgical therapy, or immunotherapy.

The terms "contacted" and "exposed," when applied to a cell, are used herein to describe the process by which a therapeutic construct and a chemotherapeutic or radiotherapeutic agent are delivered to a target cell or are placed in direct juxtaposition with the target cell. To achieve cell killing, for example, both agents are delivered to a cell in a combined amount effective to kill the cell or prevent it from dividing.

An inhibitory antibody may be administered before, during, after, or in various combinations relative to an anti-cancer treatment. The administrations may be in intervals ranging from concurrently to minutes to days to weeks. In embodiments where the antibody or antibody fragment is provided to a patient separately from an anti-cancer agent, one would generally ensure that a significant period of time did not expire between the time of each delivery, such that the two compounds would still be able to exert an advantageously combined effect on the patient. In such instances, it is contemplated that one may provide a patient with the antibody therapy and the anti-cancer therapy within about 12 to 24 or 72 h of each other and, more particularly, within about 6-12 h of each other. In some situations it may be desirable to extend the time period for treatment significantly where several days (2, 3, 4, 5, 6, or 7) to several weeks (1, 2, 3, 4, 5, 6, 7, or 8) lapse between respective administrations.

In certain embodiments, a course of treatment will last 1-90 days or more (this such range includes intervening days). It is contemplated that one agent may be given on any day of day 1 to day 90 (this such range includes intervening days) or any combination thereof, and another agent is given on any day of day 1 to day 90 (this such range includes intervening days) or any combination thereof. Within a single day (24-hour period), the patient may be given one or multiple administrations of the agent(s). Moreover, after a course of treatment, it is contemplated that there is a period of time at which no anti-cancer treatment is administered. This time period may last 1-7 days, and/or 1-5 weeks, and/or 1-12 months or more (this such range includes intervening days), depending on the condition of the patient, such as their prognosis, strength, health, etc. It is expected that the treatment cycles would be repeated as necessary.

Various combinations may be employed. For the example below an antibody therapy is "A" and an anti-cancer therapy is "B":

| | | | | | | | |
|---|---|---|---|---|---|---|---|
| A/B/A | B/A/B | B/B/A | A/A/B | A/B/B | B/A/A | A/B/B/B | B/A/B/B |
| B/B/B/A | B/B/A/B | A/A/B/B | A/B/A/B | A/B/B/A | B/B/A/A | | |
| B/A/B/A | B/A/A/B | A/A/A/B | B/A/A/A | A/B/A/A | A/A/B/A | | |

Administration of any compound or therapy of the present embodiments to a patient will follow general protocols for the administration of such compounds, taking into account the toxicity, if any, of the agents. Therefore, in some embodiments there is a step of monitoring toxicity that is attributable to combination therapy.

1. Chemotherapy

A wide variety of chemotherapeutic agents may be used in accordance with the present embodiments. The term "chemotherapy" refers to the use of drugs to treat cancer. A "chemotherapeutic agent" is used to connote a compound or composition that is administered in the treatment of cancer. These agents or drugs are categorized by their mode of activity within a cell, for example, whether and at what stage they affect the cell cycle. Alternatively, an agent may be characterized based on its ability to directly cross-link DNA, to intercalate into DNA, or to induce chromosomal and mitotic aberrations by affecting nucleic acid synthesis.

Examples of chemotherapeutic agents include alkylating agents, such as thiotepa and cyclosphosphamide; alkyl sulfonates, such as busulfan, improsulfan, and piposulfan; aziridines, such as benzodopa, carboquone, meturedopa, and uredopa; ethylenimines and methylamelamines, including altretamine, triethylenemelamine, trietylenephosphoramide, triethiylenethiophosphoramide, and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards, such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, and uracil mustard; nitrosureas, such as carmustine, chlorozotocin, fotemustine, lomustine, nimustine, and ranimnustine; antibiotics, such as the enediyne antibiotics (e.g., calicheamicin, especially calicheamicin gammaI1 and calicheamicin omegaI1); dynemicin, including dynemicin A; bisphosphonates, such as clodronate; an esperamicin; as well as neocarzinostatin chromophore and related chromoprotein enediyne antibiotic chromophores, aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins, such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, and zorubicin; anti-metabolites, such as methotrexate and 5-fluorouracil (5-FU); folic acid analogues, such as denopterin, pteropterin, and trimetrexate; purine analogs, such as fludarabine, 6-mercaptopurine, thiamiprine, and thioguanine; pyrimidine analogs, such as ancitabine, azacitidine, 6-azauridine, carmofur, cytarabine, dideoxyuridine, doxifluridine, enocitabine, and floxuridine; androgens, such as calusterone, dromostanolone propionate, epitiostanol, mepitiostane, and testolactone; anti-adrenals, such as mitotane and trilostane; folic acid replenisher, such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids, such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSKpolysaccharide complex; razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; taxoids, e.g., paclitaxel and docetaxel gemcitabine; 6-thioguanine; mercaptopurine; platinum coordination complexes, such as cisplatin, oxaliplatin, and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-11); topoisomerase inhibitor RFS 2000; difluorometlhylornithine (DMFO); retinoids, such as retinoic acid; capecitabine; carboplatin, procarbazine, plicomycin, gemcitabien, navelbine, farnesyl-protein transferase inhibitors, transplatinum, and pharmaceutically acceptable salts, acids, or derivatives of any of the above.

2. Radiotherapy

Other factors that cause DNA damage and have been used extensively include what are commonly known as γ-rays, X-rays, and/or the directed delivery of radioisotopes to tumor cells. Other forms of DNA damaging factors are also contemplated, such as microwaves, proton beam irradiation (U.S. Pat. Nos. 5,760,395 and 4,870,287), and UV-irradiation. It is most likely that all of these factors affect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

3. Immunotherapy

The skilled artisan will understand that additional immunotherapies may be used in combination or in conjunction with methods of the embodiments. In the context of cancer treatment, immunotherapeutics, generally, rely on the use of immune effector cells and molecules to target and destroy cancer cells. The immune effector may be, for example, comprise an antibody or chimeric antigen receptor (CAR) specific for some marker on the surface of a tumor cell. In further aspects, the therapy may comprise administration of T-cell or NK-cells that are targeted to specific cancer cell. Such cells can be engineered or merely selected for anti-cancer cell activity.

In some aspects, an antibody alone may serve as an effector of therapy or it may recruit other cells to actually affect cell killing. The antibody also may be conjugated to a drug or toxin (chemotherapeutic, radionuclide, ricin A chain, cholera toxin, pertussis toxin, etc.) and serve as a targeting agent. Alternatively, the effector may be a lymphocyte carrying a surface molecule that interacts, either directly or indirectly, with a tumor cell target. Various effector cells include cytotoxic T cells and NK cells Antibody-drug conjugates have emerged as a breakthrough approach to the development of cancer therapeutics. Cancer is one of the leading causes of deaths in the world. Antibody-drug conjugates (ADCs) comprise monoclonal antibodies (MAbs) that are covalently linked to cell-killing drugs. This approach combines the high specificity of MAbs against their antigen targets with highly potent cytotoxic drugs, resulting in "armed" MAbs that deliver the payload (drug) to tumor cells with enriched levels of the antigen. Targeted delivery of the drug also minimizes its exposure in normal tissues, resulting in decreased toxicity and improved therapeutic index. The approval of two ADC drugs, ADCE-TRIS® (brentuximab vedotin) in 2011 and KADCYLA® (trastuzumab emtansine or T-DM1) in 2013 by FDA validated the approach. There are currently more than 30 ADC drug candidates in various stages of clinical trials for cancer treatment. As antibody engineering and linker-payload optimization are becoming more and more mature, the discovery and development of new ADCs are increasingly dependent on the identification and validation of new targets that are suitable to this approach and the generation of targeting MAbs. Two criteria for ADC targets are upregulated/high levels of expression in tumor cells and robust internalization.

In one aspect of immunotherapy, the tumor cell must bear some marker that is amenable to targeting, i.e., is not present on the majority of other cells. Many tumor markers exist and any of these may be suitable for targeting in the context of the present embodiments. Common tumor markers include CD20, carcinoembryonic antigen, tyrosinase (p97), gp68, TAG-72, HMFG, Sialyl Lewis Antigen, MucA, MucB, PLAP, laminin receptor, erb B, and p155. An alternative aspect of immunotherapy is to combine anticancer effects with immune stimulatory effects. Immune stimulating molecules also exist including: cytokines, such as IL-2, IL-4, IL-12, GM-CSF, gamma-IFN, chemokines, such as MIP-1, MCP-1, IL-8, and growth factors, such as FLT3 ligand.

Examples of immunotherapies currently under investigation or in use are immune adjuvants, e.g., *Mycobacterium bovis, Plasmodium falciparum*, dinitrochlorobenzene, and aromatic compounds (U.S. Pat. Nos. 5,801,005 and 5,739, 169; Hui and Hashimoto, 1998; Christodoulides et al., 1998); cytokine therapy. e.g., interferons α, β, and γ, IL-1, GM-CSF, and TNF (Bukowski et al., 1998; Davidson et al., 1998; Hellstrand et al., 1998); gene therapy, e.g., TNF, IL-1, IL-2, and p53 (Qin et al., 1998; Austin-Ward and Villaseca, 1998; U.S. Pat. Nos. 5,830,880 and 5,846,945); and monoclonal antibodies. e.g., anti-CD20, anti-ganglioside GM2, and anti-p185 (Hollander, 2012; Hanibuchi et al., 1998; U.S.

Pat. No. 5,824,311). It is contemplated that one or more anti-cancer therapies may be employed with the antibody therapies described herein.

In some embodiments, the immunotherapy may be an immune checkpoint inhibitor. Immune checkpoints are molecules in the immune system that either turn up a signal (e.g., co-stimulatory molecules) or turn down a signal. Inhibitory checkpoint molecules that may be targeted by immune checkpoint blockade include adenosine A2A receptor (A2AR), B7-H3 (also known as CD276). B and T lymphocyte attenuator (BTLA), cytotoxic T-lymphocyte-associated protein 4 (CTLA-4, also known as CD152), indoleamine 2,3-dioxygenase (IDO), killer-cell immunoglobulin (KIR), lymphocyte activation gene-3 (LAG3), programmed death 1 (PD-1), T-cell immunoglobulin domain and mucin domain 3 (TIM-3) and V-domain Ig suppressor of T cell activation (VISTA). In particular, the immune checkpoint inhibitors target the PD-1 axis and/or CTLA-4.

The immune checkpoint inhibitors may be drugs such as small molecules, recombinant forms of ligand or receptors, or, in particular, are antibodies, such as human antibodies (e.g., International Patent Publication WO2015016718; Pardoll, 2012; both incorporated herein by reference). Known inhibitors of the immune checkpoint proteins or analogs thereof may be used, in particular chimerized, humanized or human forms of antibodies may be used. As the skilled person will know, alternative and/or equivalent names may be in use for certain antibodies mentioned in the present disclosure. Such alternative and/or equivalent names are interchangeable in the context of the present invention. For example, it is known that lambrolizumab is also known under the alternative and equivalent names MK-3475 and pembrolizumab.

In some embodiments, the PD-1 binding antagonist is a molecule that inhibits the binding of PD-1 to its ligand binding partners. In a specific aspect, the PD-1 ligand binding partners are PDL1 and/or PDL2. In another embodiment, a PDL1 binding antagonist is a molecule that inhibits the binding of PDL1 to its binding partners. In a specific aspect, PDL1 binding partners are PD-1 and/or B7-1. In another embodiment, the PDL2 binding antagonist is a molecule that inhibits the binding of PDL2 to its binding partners. In a specific aspect, a PDL2 binding partner is PD-1. The antagonist may be an antibody, an antigen binding fragment thereof, an immunoadhesin, a fusion protein, or oligopeptide. Exemplary antibodies are described in U.S. Pat. Nos. 8,735,553, 8,354,509, and 8,008,449, all incorporated herein by reference. Other PD-1 axis antagonists for use in the methods provided herein are known in the art such as described in U.S. Patent Application No. US20140294898, US2014022021, and US20110008369, all incorporated herein by reference.

In some embodiments, the PD-1 binding antagonist is an anti-PD-1 antibody (e.g., a human antibody, a humanized antibody, or a chimeric antibody). In some embodiments, the anti-PD-1 antibody is selected from the group consisting of nivolumab, pembrolizumab, and CT-011. In some embodiments, the PD-1 binding antagonist is an immunoadhesin (e.g., an immunoadhesin comprising an extracellular or PD-1 binding portion of PDL1 or PDL2 fused to a constant region (e.g., an Fc region of an immunoglobulin sequence). In some embodiments, the PD-1 binding antagonist is AMP-224, Nivolumab, also known as MDX-1106-04, MDX-1106, ONO-4538, BMS-936558, and OPDIVO*, is an anti-PD-1 antibody described in WO2006/121168, Pembrolizumab, also known as MK-3475, Merck 3475, lambrolizumab, KEYTRUDA®, and SCH-900475, is an anti-PD-1 antibody described in WO2009/114335, CT-011, also known as hBAT or hBAT-1, is an anti-PD-1 antibody described in WO2009/101611, AMP-224, also known as B7-DCIg, is a PDL2-Fc fusion soluble receptor described in WO2010/027827 and WO2011/066342.

Another immune checkpoint that can be targeted in the methods provided herein is the cytotoxic T-lymphocyte-associated protein 4 (CTLA-4), also known as CD152. The complete cDNA sequence of human CTLA-4 has the Genbank accession number L15006. CTLA-4 is found on the surface of T cells and acts as an "off" switch when bound to CD80 or CD86 on the surface of antigen-presenting cells. CTLA4 is a member of the immunoglobulin superfamily that is expressed on the surface of Helper T cells and transmits an inhibitory signal to T cells. CTLA4 is similar to the T-cell co-stimulatory protein, CD28, and both molecules bind to CD80 and CD86, also called B7-1 and B7-2 respectively, on antigen-presenting cells. CTLA4 transmits an inhibitory signal to T cells, whereas CD28 transmits a stimulatory signal. Intracellular CTLA4 is also found in regulatory T cells and may be important to their function. T cell activation through the T cell receptor and CD28 leads to increased expression of CTLA-4, an inhibitory receptor for B7 molecules.

In some embodiments, the immune checkpoint inhibitor is an anti-CTLA-4 antibody (e.g., a human antibody, a humanized antibody, or a chimeric antibody), an antigen binding fragment thereof, an immunoadhesin, a fusion protein, or oligopeptide.

Anti-human-CTLA-4 antibodies (or VH and/or VL domains derived therefrom) suitable for use in the present methods can be generated using methods well known in the art. Alternatively, art recognized anti-CTLA-4 antibodies can be used. For example, the anti-CTLA-4 antibodies disclosed in: U.S. Pat. No. 8,119,129, WO 01/14424, WO 98/42752; WO 00/37504 (CP675,206, also known as tremelimumab; formerly ticilimumab), U.S. Pat. No. 6,207,156; Hurwitz et al. (1998) Proc Natl Acad Sci USA 95(17): 10067-10071; Camacho et al. (2004) J Clin Oncology 22(145): Abstract No. 2505 (antibody CP-675206); and Mokyr et al. (1998) Cancer Res 58:5301-5304 can be used in the methods disclosed herein. The teachings of each of the aforementioned publications are hereby incorporated by reference. Antibodies that compete with any of these art-recognized antibodies for binding to CTLA-4 also can be used. For example, a humanized CTLA-4 antibody is described in International Patent Application No. WO2001014424, WO2000037504, and U.S. Pat. No. 8,017, 114; all incorporated herein by reference.

An exemplary anti-CTLA-4 antibody is ipilimumab (also known as 10D1, MDX-010, MDX-101, and Yervoy®) or antigen binding fragments and variants thereof (see, e.g., WOO 1/14424). In other embodiments, the antibody comprises the heavy and light chain CDRs or VRs of ipilimumab. Accordingly, in one embodiment, the antibody comprises the CDR1, CDR2, and CDR3 domains of the VH region of ipilimumab, and the CDR1, CDR2 and CDR3 domains of the VL region of ipilimumab. In another embodiment, the antibody competes for binding with and/or binds to the same epitope on CTLA-4 as the above-mentioned antibodies. In another embodiment, the antibody has at least about 90% variable region amino acid sequence identity with the above-mentioned antibodies (e.g., at least about 90%, 95%, or 99% variable region identity with ipilimumab).

Other molecules for modulating CTLA-4 include CTLA-4 ligands and receptors such as described in U.S. Pat.

Nos. 5,844,905, 5,885,796 and International Patent Application Nos. WO1995001994 and WO1998042752; all incorporated herein by reference, and immunoadhesions such as described in U.S. Pat. No. 8,329,867, incorporated herein by reference.

4. Surgery

Approximately 60% of persons with cancer will undergo surgery of some type, which includes preventative, diagnostic or staging, curative, and palliative surgery. Curative surgery includes resection in which all or part of cancerous tissue is physically removed, excised, and/or destroyed and may be used in conjunction with other therapies, such as the treatment of the present embodiments, chemotherapy, radiotherapy, hormonal therapy, gene therapy, immunotherapy, and/or alternative therapies. Tumor resection refers to physical removal of at least part of a tumor. In addition to tumor resection, treatment by surgery includes laser surgery, cryosurgery, electrosurgery, and microscopically-controlled surgery (Mohs' surgery).

Upon excision of part or all of cancerous cells, tissue, or tumor, a cavity may be formed in the body. Treatment may be accomplished by perfusion, direct injection, or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

5. Other Agents

It is contemplated that other agents may be used in combination with certain aspects of the present embodiments to improve the therapeutic efficacy of treatment. These additional agents include agents that affect the upregulation of cell surface receptors and GAP junctions, cytostatic and differentiation agents, inhibitors of cell adhesion, agents that increase the sensitivity of the hyperproliferative cells to apoptotic inducers, or other biological agents. Increases in intercellular signaling by elevating the number of GAP junctions would increase the anti-hyperproliferative effects on the neighboring hyperproliferative cell population. In other embodiments, cytostatic or differentiation agents can be used in combination with certain aspects of the present embodiments to improve the anti-hyperproliferative efficacy of the treatments. Inhibitors of cell adhesion are contemplated to improve the efficacy of the present embodiments. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with certain aspects of the present embodiments to improve the treatment efficacy.

III. Kits and Diagnostics

In various aspects of the embodiments, a kit is envisioned containing therapeutic agents and/or other therapeutic and delivery agents. In some embodiments, the present embodiments contemplates a kit for preparing and/or administering a therapy of the embodiments. The kit may comprise one or more sealed vials containing any of the pharmaceutical compositions of the present embodiments. The kit may include, for example, at least one 4-1BB antibody as well as reagents to prepare, formulate, and/or administer the components of the embodiments or perform one or more steps of the inventive methods. In some embodiments, the kit may also comprise a suitable container, which is a container that will not react with components of the kit, such as an eppendorf tube, an assay plate, a syringe, a bottle, or a tube. The container may be made from sterilizable materials such as plastic or glass.

The kit may further include an instruction sheet that outlines the procedural steps of the methods set forth herein, and will follow substantially the same procedures as described herein or are known to those of ordinary skill in the art. The instruction information may be in a computer readable media containing machine-readable instructions that, when executed using a computer, cause the display of a real or virtual procedure of delivering a pharmaceutically effective amount of a therapeutic agent.

IV. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—Production and Characterization of Anti-41BB Antibodies

Figure 1A:
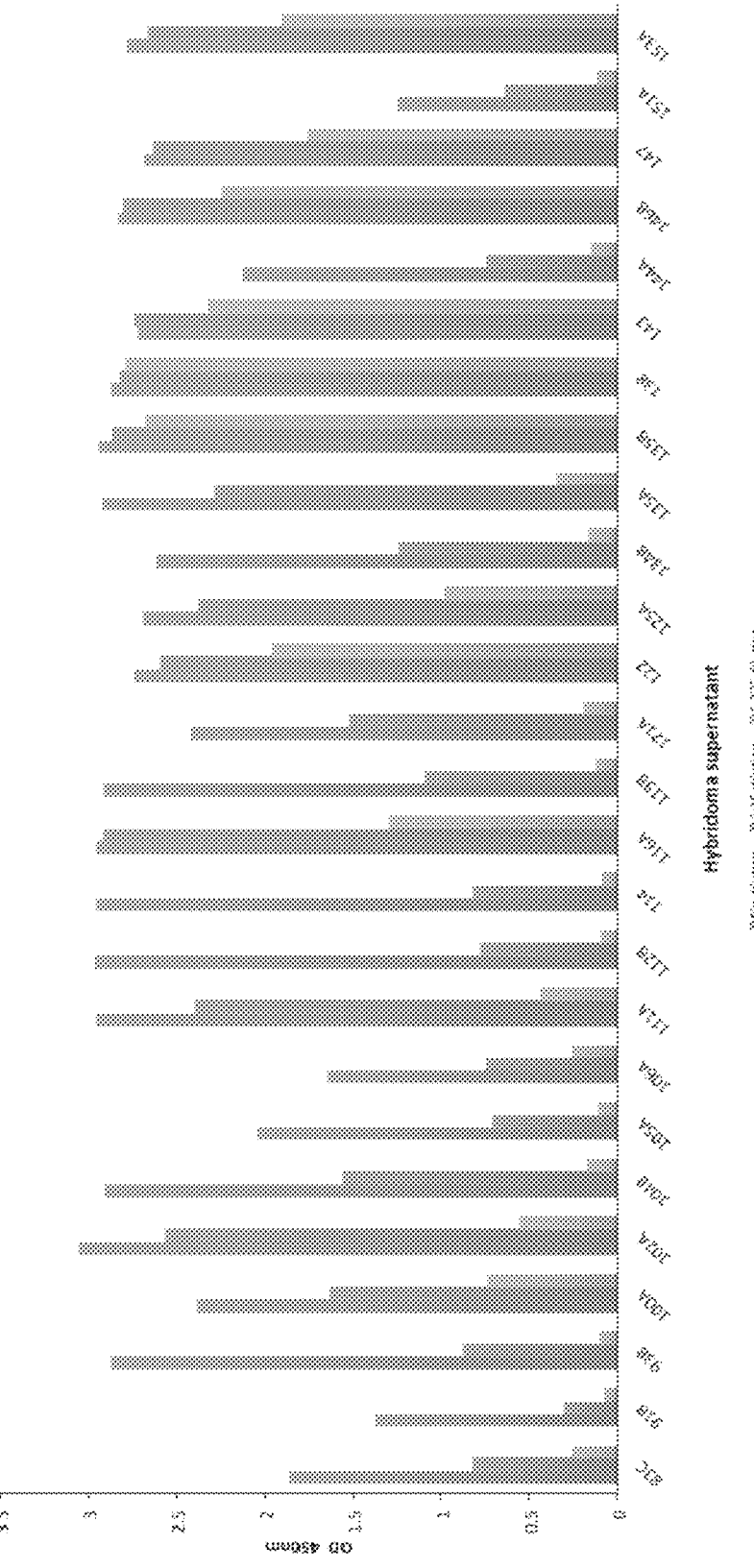
Figure 1B:
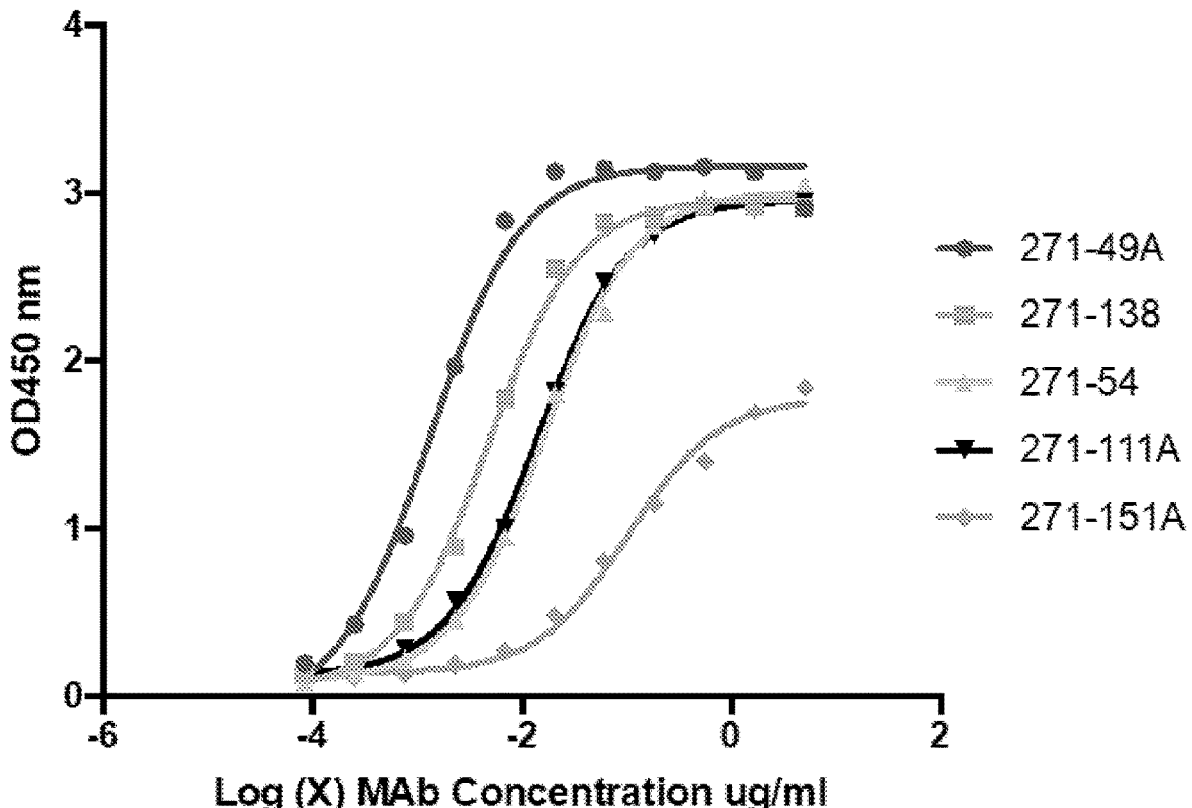

Mice were immunized with alternating cellular (macrophages or dendritic cells retrovirally engineered to express 4-1BB) and recombinant protein-based (recombinant human 4-1BB extracellular region with Fc or HIS tag) vaccines in order to generate antibodies targeting human 4-1BB (FIG. 1), including Clone 54 (IgG2a), Clone 49A (IgG1), Clone 138 (IgG2b), Clone 151 (IgG3), and Clone 111A (IgG1). A titration curve of the clones was performed by ELISA and EC50 values were determined (FIG. 1B).

RNA extraction: Hybridoma cell pellets were provided by Long Vien (Monoclonal Antibody Core Facility MDACC). Total mRNA was extracted from the hybridoma cell pellets. Total RNA was extracted from the hybridoma clone 271-54 41-BB cell pellet using RNA extraction protocol (Zymo Research).

Figure 3:
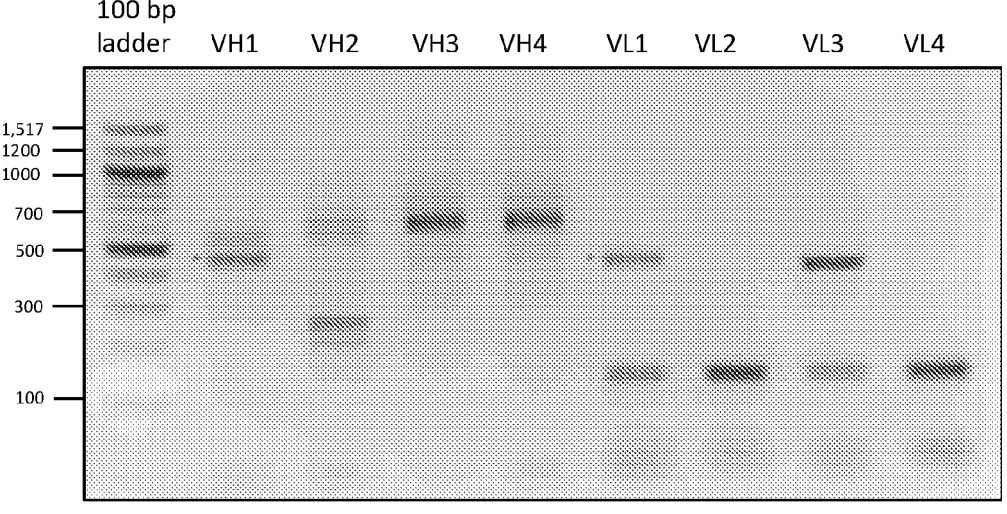
FIG. 3: PCR using several combinations of Ig variable domain primers. The asterisk shows the correct antibody transcript for the VH and VL chains. The remaining PCR bands observed are aberrant transcripts confirmed by sequencing.

RT-PCR: cDNA was created from the RNA by reverse-transcription with random primers (RT SuperscritIII, Life Technologies). PCR reactions using variable domain primers to amplify both the VH and VL regions of the monoclonal antibody DNA giving the bands in FIG. 3. The VH and VL products were gel purified and cloned into the sequencing vector pCR™2.1-TOPO® and transformed into DH5a cells. Next, positive transformants were screened for by PCR using M16 forward and reverse primers (mFVIj Forward primer (position 59-76) sequence: ACTGCAGGTGTCCTCTCT (SEQ ID NO: 65); mRevIgG2a Reverse primer (position 526-506) sequence: TAACCCTTGACCAGGCATCC (SEQ ID NO: 66); mFVK4/5a Forward primer (position 47-67) sequence: TCAGCTTCYTGCTAATCAGTG (SEQ ID NO:67); 1mRK Reverse primer (position 491-471) sequence: ACTGAGGCACCTCCAGATGTT (SEQ ID NO:68)). Selected colonies were picked for mini prep plasmid purification and analyzed by DNA sequencing (MDACC core facility).

Figure 2A:
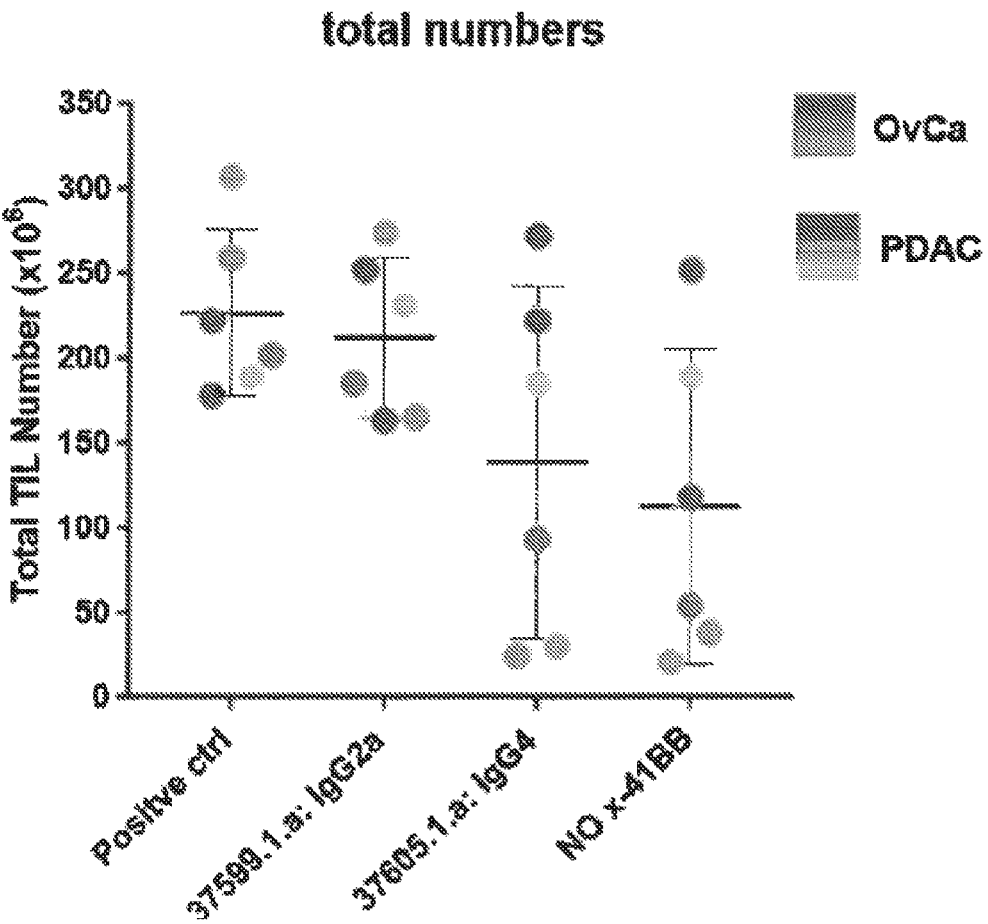
FIGS. 2A-2B: The present clone 54 4-1BB antibody (referred to herein as Curranlumab) amplifies human TIL with high efficiency. Two variants of clone 54 (Curranlumab) were used to amplify human tumor-infiltrating lymphocytes (TILs) from patient tumor chunks and the efficiency of each in generating pure, expanded CD8+ T cell products was compared to Urelumab (BMS-663513).
Figure 2B:
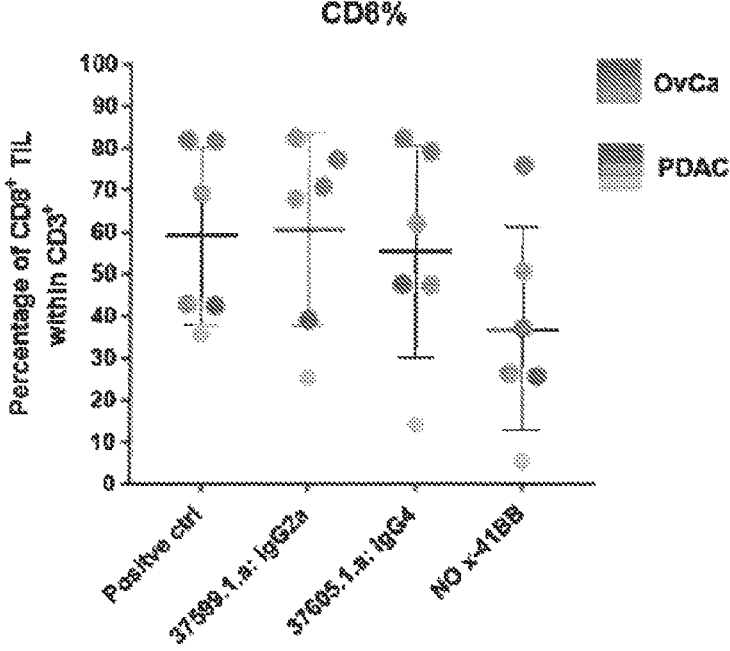
Figure 2B:
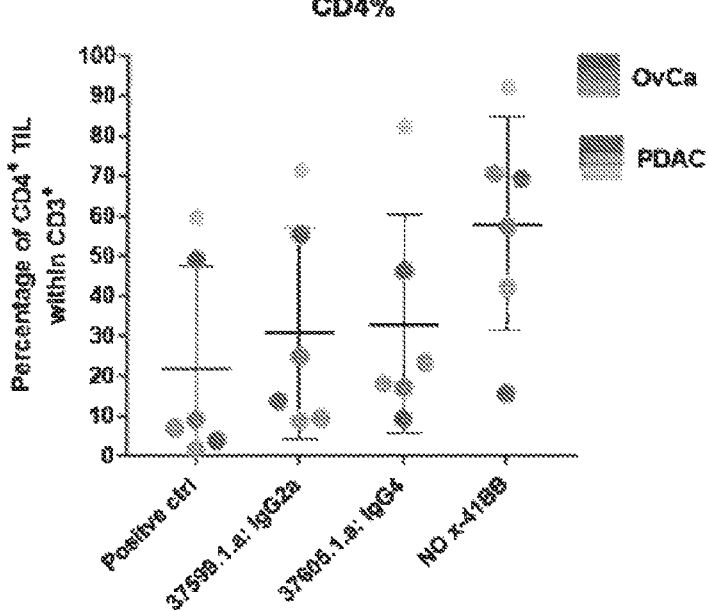
Figure 4A:
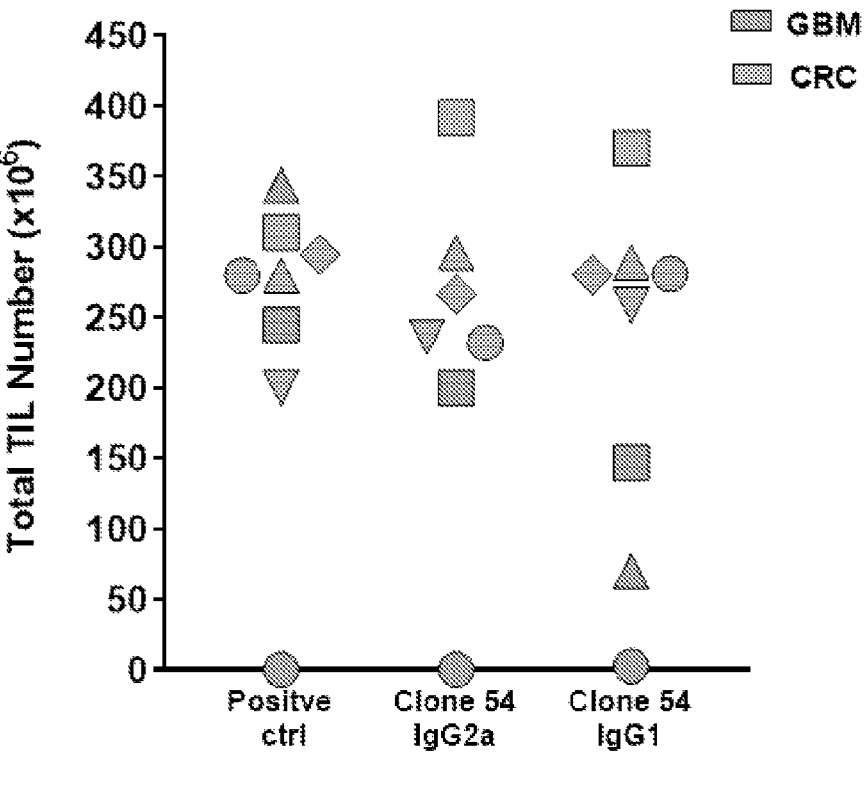
FIGS. 4A-4B: Glioblastoma and colorectal cancer tumors were isolated and tumor infiltrating T cells amplified using 41BB agonist antibody clone 54 as either human IgG1 or mouse IgG2a. Extent of amplification, percent CD8 and percent CD4 are shown. Total TILs from glioblastoma and colorectal cancer patient tumors amplified with Clone 54 IgG1 and Clone 54 IgG1 (FIG. 4A). Percentage of CD3+ CD8+ TILs or CD3+CD4+ TILs generated by expansion method (FIG. 4B).
Figure 4B:
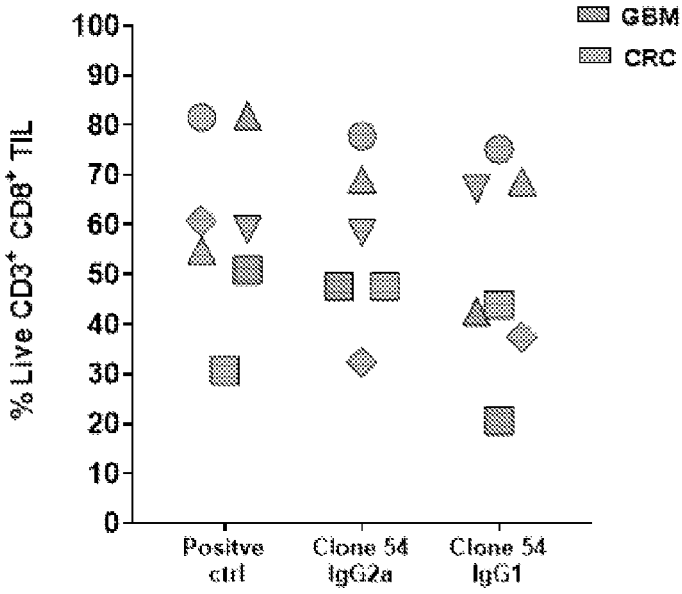
Figure 4B:
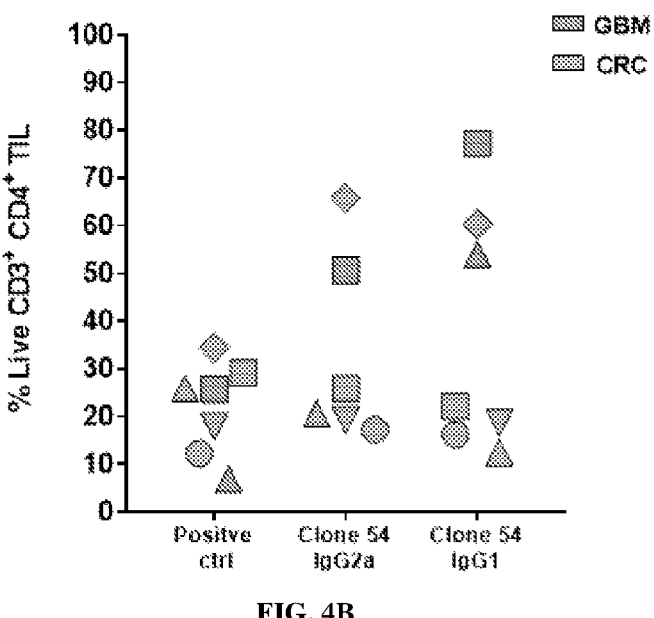

Among many lead candidates, the clone 54 4-1BB antibody was selected which was sequenced and expressed in a variety of mouse and human isotypes. Patient tumor chunks were cultured in tumor-infiltrating lymphocyte media to support their survival and rapid proliferation in cell culture. The present studies found that the mouse IgG2a version of clone 54 4-1BB antibody amplified and matured human tumor infiltrating CD8 T cells and CD4 T cells as efficiently as the anti-human 4-1BB antibody urelumab (FIG. 2B). In addition, clone 54 efficiently amplified tumor infiltrating CD8 T cells and CD4 T cells from tumors of patients with glioblastoma or colorectal cancer (FIG. 4).

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Austin-Ward and Villaseca, *Revista Medica de Chile*, 126 (7):838-845, 1998.
Bukowski et al., *Clinical Cancer Res.*, 4(10):2337-2347, 1998.
Christodoulides et al., *Microbiology*, 144(Pt 11):3027-3037, 1998.
Davidson et al., *J. Immunother.*, 21(5):389-398, 1998.
Hanibuchi et al., *Int. J. Cancer*, 78(4):480-485, 1998.
Hellstrand et al., *Acta Oncologica*, 37(4):347-353, 1998.
Hollander, *Front. Immun.*, 3:3, 2012.
Hui and Hashimoto. *Infection Immun.*, 66(11):5329-5336, 1998.
International Patent Publication No. WO2009/101611
International Patent Publication No. WO2010/027827
International Patent Publication No. WO2011/066342
International Patent Publication No. WO2015016718
Pardoll, *Nature Rev Cancer*, 12:252-264, 2012.
Qin et al., *Proc. Natl. Acad. Sci. USA*, 95(24):14411-14416, 1998.
U.S. Pat. No. 4,870,287
U.S. Pat. No. 5,091,513
U.S. Pat. No. 5,739,169
U.S. Pat. No. 5,760,395
U.S. Pat. No. 5,801,005
U.S. Pat. No. 5,824,311
U.S. Pat. No. 5,830,880
U.S. Pat. No. 5,846,945
U.S. Pat. No. 6,881,557
U.S. Pat. No. 8,008,449
U.S. Pat. No. 8,354,509
U.S. Pat. No. 8,735,553
U.S. Patent Publication No. US20050214860
U.S. Patent Publication No. US20110008369
U.S. Patent Publication No. US2014022021
U.S. Patent Publication No. US20140294898
Vinay and Kwon, Mol Cancer Ther, 11(5): 1062-70, 2012.

What is claimed is:

1. An isolated monoclonal antibody, wherein the antibody specifically binds to 4-1BB and comprises:
   (a) a first $V_H$ CDR is identical to SEQ ID NO: 3;
   (b) a second $V_H$ CDR is identical to SEQ ID NO: 5;
   (c) a third $V_H$ CDR is identical to SEQ ID NO: 7;
   (d) a first $V_L$ CDR is identical to SEQ ID NO: 11;
   (e) a second $V_L$ CDR is identical to SEQ ID NO: 13; and
   (f) a third $V_L$ CDR is identical to SEQ ID NO: 15; or
   (a) a first $V_H$ CDR is identical to SEQ ID NO: 19;
   (b) a second $V_H$ CDR is identical to SEQ ID NO: 21;
   (c) a third $V_H$ CDR is identical to SEQ ID NO: 23;
   (d) a first $V_L$ CDR is identical to SEQ ID NO: 27;
   (e) a second $V_L$ CDR is identical to SEQ ID NO: 29; and (f) a third $V_L$ CDR is identical to SEQ ID NO: 31; or
(a) a first $V_H$ CDR is identical to SEQ ID NO: 35;
(b) a second $V_H$ CDR is identical to SEQ ID NO: 37;
(c) a third $V_H$ CDR is identical to SEQ ID NO: 39;
(d) a first $V_L$ CDR is identical to SEQ ID NO: 43;
(e) a second $V_L$ CDR is identical to SEQ ID NO: 45; and
(f) a third $V_L$ CDR is identical to SEQ ID NO: 47; or
(a) a first $V_H$ CDR is identical to SEQ ID NO: 51;
(b) a second $V_H$ CDR is identical to SEQ ID NO: 53;
(c) a third $V_H$ CDR is identical to SEQ ID NO: 55;
(d) a first $V_L$ CDR is identical to SEQ ID NO: 59;
(e) a second $V_L$ CDR is identical to SEQ ID NO: 61; and
(f) a third $V_L$ CDR is identical to SEQ ID NO: 63.

2. The antibody of claim 1, wherein the antibody comprises:
(a) a first $V_H$ CDR is identical to SEQ ID NO: 3;
(b) a second $V_H$ CDR is identical to SEQ ID NO: 5;
(c) a third $V_H$ CDR is identical to SEQ ID NO: 7;
(d) a first $V_L$ CDR is identical to SEQ ID NO: 11;
(e) a second $V_L$ CDR is identical to SEQ ID NO: 13; and
(f) a third $V_L$ CDR is identical to SEQ ID NO: 15.

3. The antibody of claim 2, wherein the antibody comprises a $V_H$ domain at least about 90% identical to the $V_H$ domain of clone 54 (SEQ ID NO: 2) and a $V_L$ domain at least about 90% identical to the $V_L$ domain of clone 54 (SEQ ID NO: 10).

4. The antibody of claim 2, wherein the antibody comprises a $V_H$ domain identical to the $V_H$ domain of clone 54 (SEQ ID NO: 2) and a $V_L$ domain identical to the $V_L$ domain of clone 54 (SEQ ID NO: 10).

5. The antibody of claim 1, wherein the antibody comprises:
(a) a first $V_H$ CDR is identical to SEQ ID NO: 19;
(b) a second $V_H$ CDR is identical to SEQ ID NO: 21;
(c) a third $V_H$ CDR is identical to SEQ ID NO: 23;
(d) a first $V_L$ CDR is identical to SEQ ID NO: 27;
(e) a second $V_L$ CDR is identical to SEQ ID NO: 29; and
(f) a third $V_L$ CDR is identical to SEQ ID NO: 31.

6. The antibody of claim 5, wherein the antibody comprises a $V_H$ domain at least about 90% identical to the $V_H$ domain of clone 135B (SEQ ID NO: 18) and a $V_L$ domain at least about 90% identical to the $V_L$ domain of clone 135B (SEQ ID NO: 26).

7. The antibody of claim 5, wherein the antibody comprises a $V_H$ domain identical to the $V_H$ domain of clone 135B (SEQ ID NO: 18) and a $V_L$ domain identical to the $V_L$ domain of clone 135B (SEQ ID NO: 26).

8. The antibody of claim 1, wherein the antibody comprises:
(a) a first $V_H$ CDR is identical to SEQ ID NO: 35;
(b) a second $V_H$ CDR is identical to SEQ ID NO: 37;
(c) a third $V_H$ CDR is identical to SEQ ID NO: 39;
(d) a first $V_L$ CDR is identical to SEQ ID NO: 43;
(e) a second $V_L$ CDR is identical to SEQ ID NO: 45; and
(f) a third $V_L$ CDR is identical to SEQ ID NO: 47.

9. The antibody of claim 8, wherein the antibody comprises a $V_H$ domain at least about 90% identical to the $V_H$ domain of clone 138 (SEQ ID NO: 34) and a $V_L$ domain at least about 90% identical to the $V_L$ domain of clone 138 (SEQ ID NO: 42).

10. The antibody of claim 8, wherein the antibody comprises a $V_H$ domain identical to the $V_H$ domain of clone 138 (SEQ ID NO: 34) and a $V_L$ domain identical to the $V_L$ domain of clone 138 (SEQ ID NO: 42).

11. The antibody of claim 1, wherein the antibody comprises:
(a) a first $V_H$ CDR is identical to SEQ ID NO: 51;
(b) a second $V_H$ CDR is identical to SEQ ID NO: 53;
(c) a third $V_H$ CDR is identical to SEQ ID NO: 55;
(d) a first $V_L$ CDR is identical to SEQ ID NO: 59;
(e) a second $V_L$ CDR is identical to SEQ ID NO: 61; and
(f) a third $V_L$ CDR is identical to SEQ ID NO: 63.

12. The antibody of claim 11, wherein the antibody comprises a $V_H$ domain at least about 90% identical to the $V_H$ domain of clone 49A (SEQ ID NO: 50) and a $V_L$ domain at least about 90% identical to the $V_L$ domain of clone 49A (SEQ ID NO: 58).

13. The antibody of claim 11, wherein the antibody comprises a $V_H$ domain identical to the $V_H$ domain of clone 49A (SEQ ID NO: 50) and a $V_L$ domain identical to the $V_L$ domain of clone 49A (SEQ ID NO: 58).

14. The antibody of claim 1, wherein the antibody is recombinant.

15. The antibody of claim 1, wherein the antibody is an IgG, IgM, IgA or an antigen binding fragment thereof.

16. The antibody of claim 1, wherein the antibody is a Fab', a F(ab')2, a 20, F(ab')3, a monovalent scFv, or a bivalent scFv.

17. The antibody of any one of claim 1, wherein the antibody is a humanized antibody or de-immunized antibody.

18. A composition comprising an antibody of claim 1 in a pharmaceutically acceptable carrier.

19. A method for treating a subject having a cancer comprising administering an effective amount of an antibody of claim 1 to the subject.

* * * * *